(12) United States Patent
Benjamin

(10) Patent No.: US 11,234,972 B2
(45) Date of Patent: *Feb. 1, 2022

(54) METHODS OF TREATING FABRY DISEASE IN PATIENTS HAVING THE G9331A MUTATION IN THE GLA GENE

(71) Applicant: Amicus Therapeutics, Inc., Cranbury, NJ (US)

(72) Inventor: Elfrida Benjamin, Millstone Township, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/744,884

(22) Filed: Jan. 16, 2020

(65) Prior Publication Data
US 2020/0215043 A1 Jul. 9, 2020

Related U.S. Application Data

(63) Continuation of application No. 16/131,904, filed on Sep. 14, 2018, now Pat. No. 10,537,564, which is a continuation of application No. 15/459,149, filed on Mar. 15, 2017, now Pat. No. 10,076,514.

(60) Provisional application No. 62/311,511, filed on Mar. 22, 2016.

(51) Int. Cl.
*A61K 31/445* (2006.01)
*A61K 9/00* (2006.01)
*A61P 3/00* (2006.01)

(52) U.S. Cl.
CPC .......... *A61K 31/445* (2013.01); *A61K 9/0019* (2013.01); *A61K 9/0053* (2013.01); *A61P 3/00* (2018.01)

(58) Field of Classification Search
CPC ................................ A61K 31/445; A61P 3/00
See application file for complete search history.

(56) References Cited

U.S. PATENT DOCUMENTS 10,076,514 B2 * 9/2018 Benjamin ............ A61K 31/445
10,537,564 B2 * 1/2020 Benjamin ................ A61P 3/00

* cited by examiner

*Primary Examiner* — Kevin E Weddington
(74) *Attorney, Agent, or Firm* — Servilla Whitney LLC

(57) ABSTRACT

Provided are methods of treating a patient diagnosed with Fabry disease and methods of enhancing α-galactosidase A in a patient diagnosed with or suspected of having Fabry disease. Certain methods comprise administering to a patient a therapeutically effective dose of a pharmacological chaperone for α-galactosidase A, wherein the patient has a splice site mutation in intron 4 of the nucleic acid sequence encoding α-galactosidase A. Also described are uses of pharmacological chaperones for the treatment of Fabry disease and compositions for use in the treatment of Fabry disease.

19 Claims, 11 Drawing Sheets

Specification includes a Sequence Listing.

```
cccttctgtaggggcagagaggttctacttcattactgcgtctcctgggaaggccatcag      60
gactgctggctaaagtgggaaccaggactctttgtgagttaagaatttgtgtatttatat     120
gtgtgttatacacatttttaaaaaactgtaacgacatcaggttgagcagtcgtctccgg     180
gtggtgaattatgtgtatttttaaattttatactatattgttattttcaaatgttcgaa     240
attgaatatgtagattgttgttatcagcagaaaaataaacattattcaaatactctattc     300
agtaaagtaatttattgggcgcctttgtcaagcacgcatttgcctagatgtgactctaca     360
gataaaattcacttggggcctcccttacagacaatcaggcagtggagactgagtgcctg     420
aatggatagaccagcactcagaccactattttcagtatctgttttcttaactcagggcc     480
gtggttttcaaacgttttcgccttacggtcacccttagggtccccgagaccggcccag     540
acagacagatatacaaaaacacatacacagtcatgagcgtccaccatttccccaccaggc     600
gcagcacaggcggcttccggcactgagatggggggaggagggagagagcgcgaggggg     660
gaggggaaagcagagaacgaaagaggcggaggcggccccgaaccccgctctggtcttca     720
tcatcaccaccctgggtcccagttccacccacacaccaacctctaacgataccgggt     780
aattttcctccttcttccctcaaacggctatagcgagacggtagacgacgaccagaacta     840
cttctgctcacgtaagcgagtaatcacgtgagcgcctacgtcatgtgagatctcggtcac     900
gtgagcaactctcggcttaaactcgggatcactaaggtgccgcacttccttctggtatgg     960
aaataggggcgggtcaatatcaagaaaggaagagggtgattggttagcggaacgtcttacg    1020
tgactgattattggtctacctctggggataaccgtcccagttgccagagaaacaataacg    1080
tcattatttaataagtcatcggtgattggtccgcccctgaggttaatcttaaaagcccag    1140
gttacccgcggaaatttatgctgtccggtcaccgtgacaatgcagctgaggaacccagaa    1200
ctacatctgggctgcgcgcttgcgcttcgcttcctggccctcgttcctgggacatccct    1260
gggctagagcactggacaatggattggcaaggacgcctaccatgggctggctgcactgg    1320
gagcgcttcatgtgcaaccttgactgccaggaagagccagattcctgcatcaggtatcag    1380
atattgggtactcccttccctttgcttttccatgtgtttgggtgtgtttggggaactgga    1440
gagtctcaacgggaacagttgagcccgagggagagctccccacccgactctgctgctgc    1500
ttttttatccccagcaaactgtcccgaatcaggactagccctaaactttctctgtgtgac    1560
ctttcctgggatggggagtccggccagcggcccctgtttctttctctctctctctctct    1620
cgttctccttctctttctctttctcttctttcctctctcttctctctctccctgcccgg    1680
ttctcttttttcactgctccttgcagagcagggccacccataggcagtgtgcccaaagt    1740
agccctgcccggttctattcagacccttcttgtgaacttctgctcttcctctgccgggtg    1800
ctaaccgttagaacatctagggtgggtaggaggaatggggaactaagattcgtgccattt    1860
tttctccttttggggtcgtggatttctcggcagtatctcgagggagttagagagaccata    1920
aggtcgctgagatctctcccacctcgccatgagcgtggcatcaggctggaaggttgaca    1980
tggaggaactttatacatttacacctttgcgtgagggttgaggctggattagataggtat    2040
tgaacatatctgaccctcacaatccttatctgtaaattgggattacaaccttttaatttc    2100
agggagctgacaaaaaaatctgaaaatagttcttatctcacacaggtgagttttcaag    2160
gagataacctatttaaagtacatagcacagcgcttgaccattcaactgcgcttacagagc    2220
aaatgttcaatgggaaaatgaatgtaaatctacaaatctgaatgaatatgtgtattttc    2280
tggagagaggatatttaccttttcttcaaattctcaagggctctgtgatttaaaaaggt    2340
taggaatcactgatagatgttggtaaaggtggcagtcacagtacatttctgtgtccata    2400
agttattcctatgaatatctttatagataaagtcaggatgttggtcagacatcacagaag    2460
aaattggccttgtaagtttcatgtgaccctgtggtacagtatgtgtggcaattttgccca    2520
tcacggatttttttattggtatttgcatctgattataaaactaatgcatgatcattgc    2580
aaaaaatgtagataaagaagagcaaatgaaaataaagatttccccaccgttccacca    2640
cccagaaataatcatggtttaaatgttaatatacaaccttacaattgttttctatataaa    2700
tgaaaacatagatttctttatttcattattttccataaaaaatggatcatgtttatgtca    2760
tgtttggctaatggcaagaccctggcacccagtctgggctcaaattctgcctcattgtta    2820
cttagccctgtgacattgggtaaattacactttttttttttttttttttgagacgggg    2880
```

FIG. 1A

```
tctcgctctgtcgcccaggctggagtgcagtggcacgatctcggctcactgcaagtccgc    2940
ctcctgggttcacgccattcttctgcctcagcctcccgagtagctgggactacaggcgcc    3000
tgccaccacgcctggctcttttttttttttttttttttagtacagacggggtttcac      3060
catgttagccagggtggtctcaatctcctgacctcgtgattcgcccgcctcagcctccca   3120
aagtgctggtgtgagccaccgtgcccagccttacttttttttttgagagggggtctcact   3180
ctgtcacccaggttggagtgcagtggcgcgatctctgctcagtgcaaactccacctcccg   3240
gtttaagcagttctcctgtcgtagtctcctgagtagctgggattacaggcacaccacca   3300
cggccagctaattttgtattttcagtagagacgggtttcaccatgttgcccaagctggt   3360
ctcgaactcctggcctcaagtgatctgcccgccttggcctcccagagtgctgggattaca   3420
ggtgtgagccaccgcaccggcctctttttcttttagtctatcataccttgcaaata       3480
cagtggttcttcctatgtgttggttttgatatttatgtaatcaaacacatcagttttcc    3540
tttctgatttctgactttggggtcatgctgagaaagtcctttcctacctgaagataatac   3600
agtatatacgttcttactagtattttgtggattttaaaatatttaaatctttagtcc      3660
atctgaacttgttcttctatcagaaatgccacatttaataaataataagtcccatggtat   3720
cagatggctggaaggacctctttcgaaactttgttaattccattaatctgtgtattctt    3780
attctaatgctaatagttccacactagcttcctttatctttttttcttttttttttt      3840
ttttgagctggagtttcgctcttgttgcccaggctggagtacaatgtcacgatctcggtt   3900
caccgcaacctccgcctcccaggttcaagcaattctcctgcctcatcctcgcgagtagct   3960
ggaattacaggcatgcgccaccacgcctagctattttgtatttttagtagagatggggtt   4020
tctccatgttggtcaggctggtctcaaactcccagcctcaggtgatctgcctgcctcggc   4080
ctcccaaaatgctgttattacaggcgtgagccaccacgcccagccttcatcttttaatga   4140
atgtacatgtatgtaatcttttaggtgaacttttgtaatgttgtgccaagttccttaaa    4200
aagccctttggaagctgggcaggtggccacgcctgtaatcccagcatttgggagtctg     4260
aggcaggtggatcacttgaggccaggagttcaagactagcctagccaaaatgcaaaaccc   4320
tgtctctactaaagatacaaaaattagccggatgcgatggcacatgcctgtaatctcagc   4380
tactcgggaggctgaggtagaagaatcgcttgaaccggggaggcagaggttgcagtgagc   4440
aagatggcgccactgcactccagcctgggtgacagagggagactccatctcaaaaaaaa    4500
aaaaaaaaaagataaaaggaaacctaagtactcttgggctttgttaaggatttttgtt     4560
aaatatacaaaggattgcagggaaaattaacttatttaatattgagtatgcttatcca    4620
agagcaaaataatatttctccatttattcaaatcatttaggagcatcatagttttaacat   4680
atgggccttgcacgtatcttaaatttatctctaggcattttaggttgttcagttgttctt   4740
gtgaatgggatcttttctccaaataggattattgttgatatctgttgattatgttaact   4800
ttgtagtttctgactttactgaactgtcttcttagatctaatactcttttcaatttcatc   4860
atatatttctcattcctatttgtttgggttttagggcgggaatattaacgggataag     4920
agagacaaagaaatctggaaaaacaattcatttacttacattgcttgtgattacta       4980
ccacactattactgggttggaaaaaattgtgaaatcccaaggtgcctaataaatgggagg   5040
tacctaagtgttcatttaatgaattgtaatgattattggaattctctttcagtgagaag    5100
ctcttcatggagatggcagagctcatggtctcagaaggctggaaggatgcaggttatgag   5160
tacctctgcattgatgactgttggatggctccccaaagagattcagaaggcagacttcag   5220
gcagaccctcagcgctttcctcatgggattcgccagctagctaattatgtgagtttatag   5280
ataatgttcttgttcattcagaggactgtaagcacttctgtacagaagcttgtttagaaa   5340
cagccctcatggccgggcgtggtggctcacgctgtaatcccaacactttgggaggccgag   5400
gcgggtggatcacctgaggtcaagagttcaagaccagcctggccaacatggtgaaacccc   5460
aactctattaaaagtacaaaaaattagctgggcatggtggtgaacgcctgtaaccccagc   5520
tacttgggaggctgaggcaggagaatcgcttgaacccaggaggtggaagtttcagtgagc   5580
tgagatcacgccattgcactctagcctgggcaacaaagagaaactccatctcaaaaaaa    5640
aaaacaaggaaaaaagaaacagccctcatgacacttagaaagtagaatagctggctgtt    5700
atctgaacattgaattgtaaggcttatcaggtggactttgcattccatcagcagacaatt   5760
```

FIG. 1B

```
tttttttttttttttttttttgagatggagtctcattctgtctcccaggctggagggcagtg        5820
gtgcgatctcggctcactgcaagctccacctcctgggttcatgccattctcctgcctcag        5880
cctcccaagtagctgggaccacaggcacccgccaccatgcccagttaattttttgtattt        5940
ttagtagagacggggtttcaccatgttagccaagatggtctcgatctcctgacctcgtga        6000
tccgcccacctcggcctcccaaagtgctgggattacaggcatgagccaccgcgcctagcc        6060
tacaaatgttttgtaatagctcttgaggcccatcttggagttctccttttgctaaaacca        6120
ctgaactctctaggaggaaaaaggaacttggttcttgacatatgtgtgcatgtatttcca        6180
tataaccttaggaagctattgcaatggtactataaactagaattttagaagatagaagg         6240
aaaatattctggagatcattgaagagaaatggagtccaacactagttaaagatgatgaag        6300
acagatttttttttttgacggagtctcgctctgtcgcccaggctggagtgcagtggcaca        6360
atctcagctcactgcaaccctccacctcttgggttcaagtgattctcctgcctcagcctc        6420
ccaagtagctgggactacaggcgcaccaccacgcccggctaattttttgtattttttagt       6480
agagacaaggtttcaccatattcgccaggctggtctcgaactcctgaccttgtaatccgc        6540
ccaccttggcctcccaaagtgctgggattacaggcatgagccaccacgccggccgatga         6600
agacagattttattcagtactaccacagtagaggaaagagccaagttcaattccaaatac        6660
aacaaagacaggtggagatttatagccaatgagcagattgaggggtcagtggatggaat         6720
atttaagaagacatcaaggg tagggagcttcttgctaaagcttcatgtacttaaacaaga       6780
agggtgggggatgagggaaattgatcagatatcaatggtggcagtattgacttagcagga        6840
ttcttgctaagaggtcttgctaggacagacataggaagccaaggtggaggtctagtcgaa        6900
aagaaggctcatcagagaagtctaactaaagtttggtcaagaagagtctttgtcaaggta        6960
aatctatcatttcctcaaaaggtaattttcaggatcccatcaggaagattagcatggct         7020
gctagctttctcctcagttctgggctatagctcacatgcctagtttgaactagctcagca        7080
gaactgggggatttattctttgtcttccaacaaactcatctggatgattttgggggtttg        7140
tggggaaaagccccc aataccctggtgaagtaaccttgtctcttccccagcctggaatgg       7200
ttctctctttctgctacctcacgattgtgcttctacaatggtgactcttttcctccctct        7260
catttcaggttcagcaaaggactgaagctagggatttatgcagatgttggaaataaaa         7320
cctgcgcaggcttccctggagttttggatactacgacattgatgcccagacctttgctg        7380
actggggagtagatctgctaaaatttgatggttgttactgtgacagtttggaaaatttgg       7440
cagatggtaatgtttcattccagagatttagccacaaaggaaagaactttgaggccatgg       7500
tagctgagccaaagaaccaatcttcagaattttaaataccctgtcacaatactggaaata       7560
attattctccatgtgccagagctcccatctcttctctttcagttcattaattaattaatt       7620
aattcatgtaaaatccatgcatacctaaccatagctaatattgtgcacttataattcaag        7680
agggctctaagagttaattagtaattgtaactctctataacatcatttaggggagtccag        7740
gttgtcaatcggtcacagagaagaagcatcttcattcctgcctttcctcaatatacaca        7800
ccatctctgcactacttcctcagaacaatcccagcagtctggaggtactttacacaatt        7860
taagcacagagcaactgcctgtccctgctgctagtttaaacatgaaccttccaggtagcc        7920
tcttcttaaaatatacagccccagctgggcatgatggctcatgcctgtaatcctagcact        7980
ttgggaggctgaggcgggtggattacttgaggtcaggagttcgagaccaccctggccaac        8040
atggtgaaaccccatctctagtaaaaatacaaaaattagctgactttggtggcacatgcc        8100
tgtaatcccagctacttgggaagctgagacagaagagtcacttgaacctgggaaacagag        8160
gttgcagtgagccaagatcgcaccactgcactccacctggatgacagactgaaccccat        8220
ctcaaaaattaaaataaaataaaataactatatatagccccagctggaaatt             8280
catttctttcccttatttacccattgttttctcatacaggttataagcacatgtccttg        8340
gccctgaataggactggcagaagcattgtgtactcctgtgagtggcctctttatatgtgg       8400
cccttcaaaaggtgagatagtgagcccagaatccaatagaactgtactgatagatagaa       8460
cttgacaacaaaggaaaccaaggtctccttcaaagtccaacgttacttactatcatccta        8520
ccatctctcccaggttccaaccacttctcaccatcccactgctgtaattatagcctaag       8580
ctaccatcacctggaaagtcatccttgtgtcttccctttatttcaccattcatgtcctg       8640
```

FIG. 1C

```
tctatcaacagtccttccaccagtatctctaaaatatctcctgaatcagcccacttcctt    8700
ccatcttcactacatgcaccctggccttccaagctactatcggctctcaaccagactgct    8760
gggaccacctgatctctctgcttccactctgtctcaaccccatctattttccaagcagc    8820
actagagttatcatattaaaatgtaaatatcagtttttttttaaagaaaaaaaccctga    8880
gacttaacagagttataaaaaatataaatgtcatcatcagttccctgcttaaaacccta    8940
actcgcttccaattgcacttggaatgaaaccaaactgcactgatccagccttgcctgcc    9000
tccccaaagtccaaggggtcatggctctttcctggctacactggttttctttctgtccc    9060
tcaacactgcaagcctattgctgccccagggcctttacacttgcttttttctgcctaga    9120
acagttcttccccaaagattttaaagggccgggctccttaacattgaagtcgcagacca    9180
aacgccacatatgcagacagttcttctctaactactttaaaatagccctctgtccattca    9240
ttcttcatcacattaacctgtttaattttcttctcagagctccacactatttggaagtat    9300
ttgttgacttgttaccatgtctccccactagagtgtaagtttcatgagggcagggacctt    9360
gtctgactttgactgtatctctcgcatatggttaagtgttaaatagttatttatggaatg    9420
aatccctattattccctcattatctctgcaaaatagtctttttctcaacatcttaaacc    9480
tgatatcccacctgcctatctacaaacttttttttgcgacagagtctcactgtcaccca    9540
ggctagagtgcagtggcgccatctcggctcactgcaacctccgcctcccgggtttaagcg    9600
attctcttgcctcagcctcccagtagctgggattataggcgtgcgctaccacatctggct    9660
aattttgtattttagtagagatggtttcaccatgttggccaggcttgtctcgaactcc    9720
tgacctcagatgatccacctgcctcggcctcccaaagtgctgggattacaggcatgagcc    9780
accgtgcccagcctctacaaacttttattccattaacaaactatatgctgggatttaag    9840
ttttctaatacttgatggagtcctatgtaattttcgagcttttaatttactaagacca    9900
ttttagttctgattatagaagtaaattaactttaagggatttcaagttatatggcctact    9960
tctgaagcaaacttcttacagtgaaaattcattataagggtttagacctccttatggaga    10020
cgttcaatctgtaaactcaagagaaggctacaagtgcctcctttaaactgttttcatctc    10080
acaaggatgttagtagaaagtaaacagaagagtcatatctgttttcacagcccaattata    10140
cagaaatccgacagtactgcaatcactggcgaaattttgctgacattgatgattcctgga    10200
aaagtataaagagtatcttggactggacatcttttaaccaggagagaattgttgatgttg    10260
ctggaccagggggttggaatgacccagatatggtaaaaacttgagccctccttgttcaag    10320
accctgcggtaggcttgtttcctattttgacattcaaggtaaatacaggtaaagttcctg    10380
ggaggaggctttatgtgagagtacttagagcaggatgctgtggaaagtggtttctccata    10440
tgggtcatctaggtaactttaagaatgtttcctcctctcttgtttgaattatttcattct    10500
ttttctcagttagtgattggcaactttggcctcagctggaatcagcaagtaactcagatg    10560
gccctctgggctatcatggctgctcctttattcatgtctaatgacctccgacacatcagc    10620
cctcaagccaaagctctccttcaggataaggacgtaattgccatcaatcaggaccccttg    10680
ggcaagcaagggtaccagcttagacaggtaaataagagtatatattttaagatggcttta    10740
tacccaataccaactttgtcttgggcctaaatctatttttttcccttgctcttgatgt    10800
tactatcagtaataaagcttcttgctagaaacattactttatttccaaaataatgctaca    10860
ggatcattttaattttcctacaagtgcttgatagttctgacattaagaatgaatgccaa    10920
actaacagggccacttatcactagttgctaagcaaccacactttcttggttttcaggga    10980
gacaactttgaagtgtgggaacgacctctctcaggcttagcctgggctgtagctatgata    11040
aaccggcaggagattggtggacctcgctcttataccatcgcagttgcttccctgggtaaa    11100
ggagtggcctgtaatcctgcctgcttcatcacacagctcctcctgtgaaaaggaagcta    11160
gggttctatgaatggacttcaaggttaagaagtcacataaatcccacaggcactgttttg    11220
cttcagctagaaaatacaatgcagatgtcattaaaagacttactttaaaatgtttatttt    11280
attgccaactactacttcctgtccaccttttctccattcactttaaaagctcaaggcta    11340
ggtggctcatgcctgtaatcccagcactttgggaggctgaggcgggcagatcacctgagg    11400
tcgggactttgagacccgcctggacaacatggtgaaacccatttctaataaaaatataa    11460
aaattagccaggtgtggtggcgcacctgtggtcccagctactctggggctgaggcatga    11520
```

FIG. 1D

```
gaatcgcttgaacccgggagtggaggttgcattgagctgagatcatgccacctcactcca      11580
gcctgggcaacaaagattccatctcaaaaaaaaaaaaaaagccaggcacagtggctcatg      11640
cctggaatcccagcacttttggaagctgaggcaggcagatcacttgaggttaggatttca      11700
agaccagcctggctaacatagtaaagccctgtctctactaaaaatacaaaaattagccag      11760
gtatggtggcgagcttctgtagccccagctactcaggagactgaggcaggagaatcactt      11820
gaacccgggaagtggggggtgcagtgacccaagatcacgccactgcattccagcctggg      11880
caacagagcaagactccatctcaaaaaaaaagttctatttccttgaataaaattttccg      11940
aagtttaaactttaggaataaaactattaaacccgtatttactcatccagatacccaccc      12000
cccttgttgagattctctcccaattatcaaaatgtgtagcatatttaactaccaagagct      12060
aaacatcattaagactgaaatgtattaagaaggatgtataggccaggcacggtgtctcac      12120
gcctgtaatcccaacactttgggaggccaagtcgggcggatcacgaggtcaggagatgga      12180
gaccatcctggccaacatggtgaaaccccctctctactaaaaatacaaaaattagccagg      12240
caggtggcaggcacctgtaatcccagctactccagaggctgaggcaggacaatcacttga      12300
acctgggaggcagaggctgcagtgagctgaggttgtaccaattgcactccagcctaggta      12360
acgagcaacactccatctcaaaaaagaaaaaaaaagatgtataatttggaactgtta      12420
agaggcattttaaaga                                                   12436
```

FIG. 1E

```
MQLRNPELHL GCALALRFLA LVSWDIPGAR ALDNGLARTP TMGWLHWERF MCNLDCQEEP  60
DSCISEKLFM EMAELMVSEG WKDAGYEYLC IDDCWMAPQR DSEGRLQADP QRFPHGIRQL 120
ANYVHSKGLK LGIYADVGNK TCAGFPGSFG YYDIDAQTFA DWGVDLLKFD GCYCDSLENL 180
ADGYKHMSLA LNRTGRSIVY SCEWPLYMWP FQKPNYTEIR QYCNHWRNFA DIDDSWKSIK 240
SILDWTSFNQ ERIVDVAGPG GWNDPDMLVI GNFGLSWNQQ VTQMALWAIM AAPLFMSNDL 300
RHISPQAKAL LQDKDVIAIN QDPLGKQGYQ LRQGDNFEVW ERPLSGLAWA VAMINRQEIG 360
GPRSYTIAVA SLGKGVACNP ACFITQLLPV KRKLGFYEWT SRLRSHINPT GTVLLQLENT 420
MQMSLKDLL                                                        429
```

FIG. 2

```
agagacaaaaaaaaatctggaaaaacaattcatttaccttacattgcttgtgattacta     4980
```

FIG. 3

METHODS OF TREATING FABRY DISEASE IN PATIENTS HAVING THE G9331A MUTATION IN THE GLA GENE

CROSS-REFERENCE TO RELATED APPLICATIONS

This is a continuation of U.S. application Ser. No. 16/131,904, filed Sep. 14, 2018, which is a continuation of U.S. application Ser. No. 15/459,149, filed Mar. 15, 2017, now U.S. Pat. No. 10,076,514, which claims the benefit under 35 U.S.C. § 119(e) to U.S. Provisional Application No. 62/311,511, filed Mar. 22, 2016, the entire contents of which are incorporated herein by reference in their entirety.

TECHNICAL FIELD

Principles and embodiments of the present invention relate generally to the use of pharmacological chaperones for the treatment of Fabry disease, particularly in patients with splice site mutations in intron 4 of the GLA gene.

BACKGROUND

Many human diseases result from mutations that cause changes in the amino acid sequence of a protein which reduce its stability and may prevent it from folding properly. Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated. The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

The majority of genetic mutations that lead to the production of less stable or misfolded proteins are called missense mutations. These mutations result in the substitution of a single amino acid for another in the protein. However, in addition to missense mutations, there are also other types of mutations that can result in proteins with reduced biological activity. Another type of mutation that can cause disease is a splice site mutation. Splice site mutations are mutations in which nucleotides are inserted, deleted or changed in number in the site where splicing of an intron takes place. This mutation can lead to incorrect processing of mRNA precursors, including exon skipping or splicing at cryptic splice points, resulting in gross structural and functional alterations.

Such mutations can lead to lysosomal storage diseases (LSDs), which are characterized by deficiencies of lysosomal enzymes due to mutations in the genes encoding the lysosomal enzymes. This results in the pathologic accumulation of substrates of those enzymes, which include lipids, carbohydrates, and polysaccharides. Although there are many different mutant genotypes associated with each LSD, many of the mutations are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

Fabry Disease is an LSD caused by a mutation to the GLA gene, which encodes the enzyme α-galactosidase A (α-Gal A). The mutation causes the substrate globotriaosylceramide (Gb3, GL-3, or ceramide trihexoside) to accumulate in various tissues and organs. Males with Fabry disease are hemizygotes because the disease genes are encoded on the X chromosome. Fabry disease is estimated to affect 1 in 40,000 and 60,000 males, and occurs less frequently in females. There have been several approaches to treatment of Fabry disease.

One approved therapy for treating Fabry disease is enzyme replacement therapy (ERT), which typically involves intravenous, infusion of a purified form of the corresponding wild-type protein (Fabrazyme®, Genzyme Corp.). One of the main complications with enzyme replacement therapy is attainment and maintenance of therapeutically effective amounts of protein in vivo due to rapid degradation of the infused protein. The current approach to overcome this problem is to perform numerous costly high dose infusions. ERT has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Gene therapy using recombinant vectors containing nucleic acid sequences that encode a functional protein, or using genetically modified human cells that express a functional protein, is also being developed to treat protein deficiencies and other disorders that benefit from protein replacement.

A third approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 related enzyme disorders called lysosomal storage disorders that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme.

Another approach to treating Fabry disease has been treatment with what are called specific pharmacological chaperones (SPCs). Such SPCs include small molecule inhibitors of α-Gal A, which can bind to the α-Gal A to increase the stability of both mutant enzyme and the corresponding wild type. However, successful candidates for SPC therapy should have a mutation which results in the production of an enzyme that has the potential to be stabilized and folded into a conformation that permits trafficking out of the ER. Mutations which severely truncate the enzyme, such as nonsense mutations, or mutations in the catalytic domain which prevent binding of the chaperone, will not be as likely to be "rescuable" or "enhanceable" using SPC therapy, i.e., to respond to SPC therapy. While missense mutations outside the catalytic site are more likely to be rescuable using SPCs, there is no guarantee, necessitating screening for responsive mutations.

Thus, even when Fabry disease is diagnosed by detecting deficient α-Gal A activity in plasma or peripheral leukocytes (WBCs), it is very difficult, if not impossible, to predict whether a particular Fabry patient will respond to treatment with an SPC. Moreover, since WBCs only survive for a short period of time in culture (in vitro), screening for SPC enhancement of α-Gal A is difficult and not optimal for the patient.

While some methods for evaluating screening patients for responsiveness to SPC therapy have been developed, these may not be applicable to all GLA mutations that cause Fabry disease. This means that there are Fabry patients who are not receiving SPC treatment because they have not been identified as treatable, although they may in fact be good candidates. Thus, there remains a need to identify new GLA mutations that will be responsive to SPC and make available new methods of treatment to Fabry patients with these mutations.

SUMMARY

One aspect of the invention pertains to a method of treating a patient diagnosed with Fabry disease. The method comprises administering to the patient a therapeutically effective dose of a pharmacological chaperone for α-galactosidase A, wherein the patient has a splice site mutation in intron 4 of the nucleic acid sequence encoding α-galactosidase A. In one or more embodiments, the mutation is G9331A relative to SEQ ID NO: 1. In some embodiments, the pharmacological chaperone comprises 1-deoxygalactonojirimycin or salt thereof. In one or more embodiments, the dose of 1-deoxygalactonojirimycin or salt thereof is from about 25 mg to about 250 mg. In some embodiments, the salt of 1-deoxygalactonojirimycin is 1-deoxygalactonojirimycin hydrochloride. In one or more embodiments, the dose is about 150 mg every other day of 1-deoxygalactonojirimycin hydrochloride or an equivalent dose of 1-deoxygalactonojirimycin or a salt thereof other than the hydrochloride salt. In some embodiments, the 1-deoxygalactonojirimycin or salt thereof is administered orally or by injection. These embodiments may be combined with one another or with other embodiments of the invention, for example embodiments relating to a method of enhancing α-galactosidase A in a patient diagnosed with or suspected of having Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease as well as embodiments relating to amenable mutations, suitable SPCs and dosages, formulations and routs of administration thereof.

Another aspect of the invention pertains to a method of enhancing α-galactosidase A in a patient diagnosed with or suspected of having Fabry disease. The method comprises administering to a patient a therapeutically effective dose of a pharmacological chaperone for α-galactosidase A, wherein the patient has a splice site mutation in intron 4 of the nucleic acid sequence encoding α-galactosidase A. In one or more embodiments, the mutation is G9331A relative to SEQ ID NO: 1. In some embodiments, the pharmacological chaperone comprises 1-deoxygalactonojirimycin or salt thereof. In one or more embodiments, the dose of 1-deoxygalactonojirimycin or salt thereof is from about 25 mg to about 250 mg. In some embodiments, the salt of 1-deoxygalactonojirimycin is 1-deoxygalactonojirimycin hydrochloride. In one or more embodiments, the dose is about 150 mg every other day of 1-deoxygalactonojirimycin hydrochloride or an equivalent dose of 1-deoxygalactonojirimycin or a salt thereof other than the hydrochloride salt. In some embodiments, the 1-deoxygalactonojirimycin or salt thereof is administered orally or by injection. These embodiments may be combined with one another or with other embodiments of the invention, for example embodiments relating to a method of treating a patient with Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease as well as embodiments relating to amenable mutations, suitable SPCs and dosages, formulations and routs of administration thereof.

Another aspect of the invention pertains to use of a pharmacological chaperone for α-galactosidase A for the manufacture of a medicament for treating a patient diagnosed with Fabry disease, wherein the patient has a splice site mutation in intron 4 of the nucleic acid sequence encoding α-galactosidase A. In one or more embodiments, the mutation is G9331A relative to SEQ ID NO: 1. In some embodiments, the pharmacological chaperone comprises 1-deoxygalactonojirimycin or salt thereof. In one or more embodiments, the dose of 1-deoxygalactonojirimycin or salt thereof is from about 25 mg to about 250 mg. In some embodiments, the salt of 1-deoxygalactonojirimycin is 1-deoxygalactonojirimycin hydrochloride. In one or more embodiments, the dose is about 150 mg every other day of 1-deoxygalactonojirimycin hydrochloride or an equivalent dose of 1-deoxygalactonojirimycin or a salt thereof other than the hydrochloride salt. In some embodiments, the 1-deoxygalactonojirimycin or salt thereof is administered orally or by injection. These embodiments may be combined with one another or with other embodiments of the invention, for example embodiments relating to a method of treating a patient with Fabry disease, a method of enhancing α-galactosidase A in a patient diagnosed with or suspected of having Fabry disease, or to a pharmacological chaperone for α-galactosidase A for use in treating a patient diagnosed with Fabry disease as well as embodiments relating to amenable mutations, suitable SPCs and dosages, formulations and routs of administration thereof.

Another aspect of the invention pertains to a pharmacological chaperone for α-galactosidase A for use in treating a patient diagnosed with Fabry disease, wherein the patient has a splice site mutation in intron 4 of the nucleic acid sequence encoding α-galactosidase A. In one or more embodiments, the mutation is G9331A relative to SEQ ID NO: 1. In some embodiments, the pharmacological chaperone comprises 1-deoxygalactonojirimycin or salt thereof. In one or more embodiments, the dose of 1-deoxygalactonojirimycin or salt thereof is from about 25 mg to about 250 mg. In some embodiments, the salt of 1-deoxygalactonojirimycin is 1-deoxygalactonojirimycin hydrochloride. In one or more embodiments, the dose is about 150 mg every other day of 1-deoxygalactonojirimycin hydrochloride or an equivalent dose of 1-deoxygalactonojirimycin or a salt thereof other than the hydrochloride salt. In some embodiments, the 1-deoxygalactonojirimycin or salt thereof is administered orally or by injection. These embodiments may be combined with one another or with other embodiments of the invention, for example embodiments relating to a method of treating a patient with Fabry disease, a method of enhancing α-galactosidase A in a patient diagnosed with or suspected of having Fabry disease or use of a pharmacological chaperone for α-galactosidase A for the manufacture of a medicament for treating a patient diagnosed with Fabry disease as well as embodiments relating to amenable mutations, suitable SPCs and dosages, formulations and routs of administration thereof.

Another aspect of the invention pertains to a pharmaceutical composition for use in the treatment of Fabry disease comprising a pharmacological chaperone for α-galactosidase A, wherein the patient has a splice site mutation in intron 4 of the nucleic acid sequence encoding α-galactosidase A.

Various embodiments are listed below. It will be understood that the embodiments listed below may be combined not only as listed below, but in other suitable combinations in accordance with the scope of the invention.

BRIEF DESCRIPTION OF THE DRAWINGS

FIGS. 1A-E shows the full DNA sequence of human wild type GLA gene (SEQ ID NO: 1);

FIG. 2 shows the wild type GLA protein (SEQ ID NO: 2);

FIG. 3 shows a partial sequence of the GLA gene showing splice site mutation G9331A (SEQ ID NO: 3);

DETAILED DESCRIPTION

Figure 4:
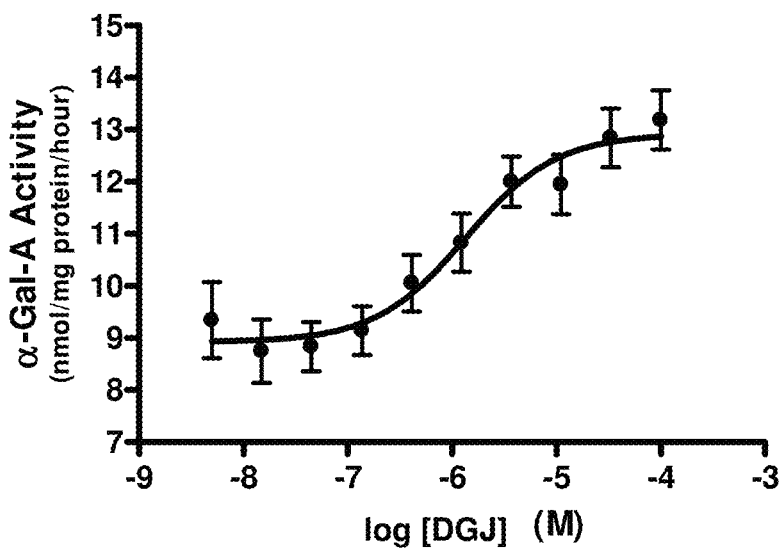
FIG. 4 shows the α-Gal A activity in mutant lymphoblasts exposed to DGJ.

Before describing several exemplary embodiments of the invention, it is to be understood that the invention is not limited to the details of construction or process steps set forth in the following description. The invention is capable of other embodiments and of being practiced or being carried out in various ways.

Various aspects of the invention pertain to identification of new GLA mutations in Fabry patients who will respond to treatment with pharmacological chaperones. Other aspects of the invention pertain to the treatment of these Fabry patients, as well. For example, it has been surprisingly discovered that the low α-Gal A activity resulting from the splice site mutation G9331A in the GLA gene can be increased when exposed to pharmacological chaperones. By extension, patients with these types of mutations will be responsive to treatment with pharmacological chaperones, where it was previously thought that patients with a splice site mutation in the GLA gene would not be responsive to treatment because splice site mutations generally cause such major changes in the enzyme.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-galactosidase A activity. This defect causes accumulation of globotriaosylceramide (ceramide trihexoside) and related glycosphingolipids in vascular endothelial lysosomes of the heart, kidneys, skin, and other tissues.

The term "atypical Fabry disease" refers to patients with primarily cardiac manifestations of the α-Gal A deficiency, namely progressive globotriaosylceramide (GL-3) accumulation in myocardial cells that leads to significant enlargement of the heart, particularly the left ventricle.

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

A "patient" refers to a subject who has been diagnosed with or is suspected of having a particular disease. The patient may be human or animal.

A "Fabry disease patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

Human α-galactosidase A (α-Gal A) refers to an enzyme encoded by the human GLA gene. The full DNA sequence of α-Gal A, including introns and exons, is available in GenBank Accession No. X14448.1 and shown in FIGS. 1A-E (SEQ ID NO: 1). The human α-Gal A enzyme consists of 429 amino acids and is available in GenBank Accession Nos. X14448.1 and U78027 and shown in FIG. 2 (SEQ ID NO: 2).

The term "mutant protein" includes a protein which has a mutation in the gene encoding the protein which results in the inability of the protein to achieve a stable conformation under the conditions normally present in the ER. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions.

As used herein in one embodiment, the term "mutant α-Gal A" includes an α-Gal A which has a mutation in the gene encoding α-Gal A which results in the inability of the enzyme to achieve a stable conformation under the conditions normally present in the ER. The failure to achieve a stable conformation results in a substantial amount of the enzyme being degraded, rather than being transported to the lysosome.

As used herein, the term "specific pharmacological chaperone" ("SPC") or "pharmacological chaperone" refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-Gal A, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones. In the present invention, the SPC may be a reversible competitive inhibitor.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

As used herein, the term "specifically binds" refers to the interaction of a pharmacological chaperone with a protein such as α-Gal A, specifically, an interaction with amino acid residues of the protein that directly participate in contacting the pharmacological chaperone. A pharmacological chaperone specifically binds a target protein, e.g., α-Gal A, to exert a chaperone effect on the protein and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-Gal A is the substrate binding site.

"Deficient α-Gal A activity" refers to α-Gal A activity in cells from a patient which is below the normal range as compared (using the same methods) to the activity in normal individuals not having or suspected of having Fabry or any other disease (especially a blood disease).

As used herein, the terms "enhance α-Gal A activity" or "increase α-Gal A activity" refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the SPC. An increase in hydrolysis is indicative of increased α-Gal A activity.

The term "α-Gal A activity" refers to the normal physiological function of a wild-type α-Gal A in a cell. For example, α-Gal A activity includes hydrolysis of GL-3.

A "responder" is an individual diagnosed with or suspected of having a lysosomal storage disorder, such as, for example Fabry disease, whose cells exhibit sufficiently increased α-Gal A activity, respectively, and/or amelioration of symptoms or improvement in surrogate markers, in response to contact with an SPC. Non-limiting examples of improvements in surrogate markers for Fabry are lyso-GB3 and those disclosed in US Patent Application Publication No. US 2010-0113517.

Non-limiting examples of improvements in surrogate markers for Fabry disease disclosed in US 2010/0113517 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin; the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Another type of clinical marker that can be assessed for Fabry disease is the prevalence of deleterious cardiovascular manifestations. Common cardiac-related signs and symptoms of Fabry disease include Left ventricular hypertrophy, valvular disease (especially mitral valve prolapse and/or regurgitation), premature coronary artery disease, angina, myocardial infarction, conduction abnormalities, arrhythmias, congestive heart failure.

The dose that achieves one or more of the aforementioned responses is a "therapeutically effective dose."

The phrase "pharmaceutically acceptable" refers to molecular entities and compositions that are physiologically tolerable and do not typically produce untoward reactions when administered to a human. In some embodiments, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" in reference to a pharmaceutical carrier refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

Pharmacological Chaperones

The binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes. This strategy has been shown to increase several lysosomal enzymes in vitro and in vivo, including β-glucocerebrosidase and α-glucosidase, deficiencies of which are associated with Gaucher and Pompe disease, respectively.

In one or more embodiments, the SPC is 1-deoxygalactonojirimycin (DGJ) which refers to a compound having the following structures:

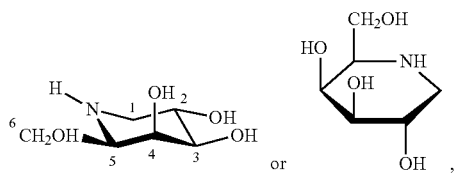

or a pharmaceutically acceptable salt, ester or prodrug of 1-deoxygalactonojirimycin. The hydrochloride salt of DGJ is known as migalastat hydrochloride (Migalastat).

Still other SPCs for α-Gal A are described in U.S. Pat. Nos. 6,274,597, 6,774,135, and 6,599,919, and include α-3,4-di-epi-homonojirimycin, 4-epi-fagomine, α-allo-homonojirimycin, N-methyl-deoxygalactonojirimycin, β-1-C-butyl-deoxygalactonojirimycin, α-galacto-homonojirimycin, calystegine $A_3$, calystegine $B_2$, calystegine $B_3$, N-methyl-calystegine $A_3$, N-methyl-calystegine $B_2$ and N-methyl-calystegine $B_3$.

In a specific embodiment, the SPC comprises 1-deoxygalactonojirimycin or salt thereof. In further embodiments, the SPC comprises 1-deoxygalactonojirimycin hydrochloride.

Any of these SPCs for α-Gal A may be used in combination with any of the other embodiments of the invention, for example embodiments relating to a method of treating a patient with Fabry disease, a method of enhancing α-galactosidase A in a patient diagnosed with or suspected of having Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease as well as embodiments relating to suitable doses of SPCs, amenable mutations and to the treatment of a Fabry patient having a splice site mutation in intron 4 of the nucleic acid sequence encoding α-galactosidase A.

Identification of GLA Mutations Responsive to Pharmacological Chaperones

Because Fabry disease is rare, involves multiple organs, has a wide age range of onset, and is heterogeneous, proper diagnosis is a challenge. Awareness is low among health care professionals and misdiagnoses are frequent. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

An "amenable mutation" as used herein means that the α-Gal A activity of a cell having the mutation will increase when incubated with a pharmacological chaperone of α-Gal A. In some embodiments, the following criteria will be met: ≥about 1.2-fold relative increase in α-Gal A activity and/or ≥about a 3.0% of wild-type (WT) absolute increase after 10 μM pharmacological chaperone incubation. In some embodiments, the pharmacological chaperone is migalastat. Any of the embodiments relating to amenable mutations can be combined with any of the other embodiments of the invention, for example embodiments relating to a method of treating a patient with Fabry disease, a method of enhancing α-galactosidase A in a patient diagnosed with or suspected of having Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease as well as embodiments relating to the SPCs, suitable dosages thereof, and to the treatment of a Fabry patient having a splice site mutation in intron 4 of the nucleic acid sequence encoding α-galactosidase A.

Previous screening methods have been provided that assess enzyme enhancement prior to the initiation of treatment. For example, an assay using HEK-293 cells has been utilized in clinical trials to predict whether a given mutation will be responsive to pharmacological chaperone (e.g., migalastat) treatment. In this assay, cDNA constructs are created. The corresponding α-Gal A mutant forms are transiently expressed in HEK-293 cells. Cells are then incubated±migalastat (17 nM to 1 mM) for 4 to 5 days. After, α-Gal A levels are measured in cell lysates using a synthetic fluorogenic substrate (4-MU-α-Gal) or by western blot. This has been done for known disease-causing missense or small in-frame insertion/deletion mutations. Mutations that have previously been identified as responsive to an SPC (e.g. DGJ) using these methods are listed in U.S. Pat. No. 8,592,362. However, this HEK-293 assay uses recombinant GLA cDNA; thus, the mutant α-Gal A is expressed independent of pre-mRNA splicing, and the HEK-293 assay cannot be used to predict response of splice site mutations.

Nevertheless, as described herein, lymphoblast assays may instead be used to identify mutations that meet the above-mentioned amenability criteria. For the splice site mutations described herein, lymphoblast cultures can be derived from male patients with the mutation, followed by the assay. Lymphoblasts may be derived by culturing in a suspension in a medium (e.g., supplemented with fetal calf serum and penicillin-streptomycin at 37° C., 5% CO2). Fabry patient lymphoblast lines can then be immortalized and established by phytohaemagglutinin stimulated Epstein-Barr virus transformation of peripheral blood mononuclear cells using blood samples. The lymphoblasts can then be seeded and incubated with varying concentrations of chaperone, and evaluated using methods known in the art (See e.g., Benjamin E. R., et al. Inherited Metab. Dis. 2009; 32:424-440).

Accordingly, another aspect of the invention pertains to a method for determining whether a Fabry disease patient will respond to treatment with a pharmacological chaperone for α-galactosidase A, wherein the patient does not have a missense mutation in an exon of the of the nucleic acid sequence encoding α-galactosidase A (SEQ ID NO: 1), the method comprising isolating genomic DNA encoding α-galactosidase A from a sample of lymphoblasts from the patient, optionally amplifying the DNA or a fragment thereof comprising intron 4 and determining the presence or absence of a splice site mutation in intron 4, wherein a patient having a splice site mutation in intron 4 is responsive to treatment with a pharmacological chaperone for α-galactosidase A.

Splice Site Mutations in Intron 4 and the Treatment of Fabry Disease

Accordingly, one or more embodiments pertains to the treatment of a Fabry patient having a splice site mutation in intron 4 of the nucleic acid sequence encoding α-galactosidase A. Because splice site mutations occur in the introns, mutations are described relative to the full GLA DNA sequence, shown in FIGS. 1A-E (SEQ ID NO: 1). Intron 4 spans nucleic acid positions 8413 through 10130 relative to SEQ ID NO: 1. One such mutation is the G9331A mutation (also known as IVS4+919G→A). An excerpt of the GLA DNA sequence showing this mutation is shown in FIG. 3 and SEQ ID NO: 3. This mutation is associated with the cardiac variant form of Fabry disease. Specifically, patients with this form of the disease may experience left-ventricular hypertrophy and have cardiomyopathy. This mutation also has shown a high prevalence among newborns (~1 in 1600 males) and patients with idiopathic hypertrophic cardiomyopathy in the Taiwan Chinese population (Lin, H., et al. Cardiovascular Genetics. 2009; 2:450-456). Indeed, the mutation was found in 82% of newborns who screened positive for Fabry disease in the Taiwan Chinese population (Id.). In the GLA gene, G9331A occurs in the middle of intron 4 (Ishii, et al. Am. J. Hum. Genet. 70:994-1002, 2002). This mutation results in the increased recognition of a normally weak splice site, resulting in the insertion of an additional 57-nucleotide sequence into the α-Gal A transcript. The inserted sequence introduces a premature termination codon downstream from exon 4, with a predicted truncated protein product of 222 amino acid residues. The abnormal α-Gal A mRNA comprised more than 70% of the total α-Gal A mRNA in lymphoblasts derived from a male Fabry patient with this mutation. However, some wild-type α-Gal A mRNA was expressed and the resultant residual α-Gal A activity was less than 10% of normal (Ishii, Nakao et al. 2002).

As shown in the examples below, the G9331A mutation was assessed for response to DGJ in a male Fabry patient derived lymphoblast assay. The male Fabry patient lymphoblast assay correlates with the HEK assay (Wu et al. Human Mutation 2011, FIG. 5), and this mutation meets the amenability criteria based on the lymphoblast assay. Because the mutation meets the aforementioned amenability criteria in the lymphoblast assay, it is thought that the mutation will show a response to DGJ in vivo. Further, the age of onset, progression, and severity of Fabry disease is at least partly dependent on the rate of substrate accumulation, which correlates to the enzymatic activity in lysosomes. Thus, a complete lack of residual activity can correspond to rapid substrate accumulation, and therefore a more severe form of the disease (having early onset and rapid progression). However, even small quantities of residual activity may be enough to degrade a large amounts of substrate. This in turn would lead to milder disease with later onset and slower progression because of the slowed. Considering these factors, it is thought that even modest increases in enzymatic activity can reduce the effect of a severe clinical phenotype. Data suggests that for most LSDs, just 1% to 6% of normal activity has been estimated as sufficient to delay or prevent disease onset or yield a more mild form of the disease. That is, just small increases in activity could have a significant impact on substrate levels, and hence disease severity and the rate of disease progression. Conversely, it is expected that a mutant lysosomal enzyme that shows no response in vitro would also not respond in vivo.

Accordingly, one aspect of the invention pertains to use of SPCs for the treatment of Fabry disease in a patient having a mutation in the gene encoding α-galactosidase A, wherein the patient is identified as having a splice site mutation in intron 4 relative to a human α-galactosidase A encoded by a nucleic acid sequence set forth in SEQ ID NO: 1. Another aspect of the invention pertains a method of treating a patient diagnosed with Fabry disease. In one or more embodiments, the method comprises administering to a patient a therapeutically effective dose of a pharmacological chaperone (SPC) of α-Gal A. In further embodiments, the patient has a splice site mutation in intron 4 of the nucleic acid sequence encoding α-galactosidase A. Another aspect of the invention pertains to a method of enhancing α-galactosidase A in a patient diagnosed with or suspected of having Fabry disease. In one or more embodiments, the method comprises administering to a patient a therapeutically effective dose of a pharmacological chaperone (SPC) of α-Gal A, wherein the patient has a mutant α-galactosidase A encoded by a nucleic acid sequence having a splice site mutation relative to SEQ ID NO: 1. Details and further embodiments of these uses and methods follows below. Any of the embodiments relating a method of treating a patient with Fabry disease, a method of enhancing α-galactosidase A in a patient diagnosed with or suspected of having Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease wherein the patient is identified as having a splice site mutation in intron 4 relative to a human α-galactosidase A encoded by a nucleic acid sequence set forth in SEQ ID NO: 1 can be combined with any of the other embodiments of the invention, for example embodiments relating to the SPCs and suitable dosages thereof.

In one or more embodiments, the patient may have other mutations in their GLA gene. For example, there may be other mutations in the intron region which may or may not affect the resulting α-Gal A enzyme. Thus, in one or more embodiments, the patient has mutant α-galactosidase A encoded by a nucleic acid sequence having 95, 96, 97, 98, 99 or 99.5% identity to SEQ ID NO: 1. In some embodiments, the patient has a mutation consisting essentially of G9331A relative to SEQ ID NO: 1. Again, any of these embodiments can be combined with any of the other embodiments of the invention, for example embodiments relating to amenable mutations, the SPCs and suitable dosages thereof.

It is unexpected that pharmacological chaperones would be effective to treat Fabry disease due to such splice site mutations. As discussed above, it is not even possible to test such mutations via the standard HEK-293 assay to determine responsiveness to incubation with pharmacological chaperone. Moreover, with respect to G9331A, it had been previously thought that the G9331A mutation was unresponsive to treatment with DGJ (See Benjamin E. R., et al. Inherited Metab. Dis. 2009; 32:424-440). Furthermore, the amenability of G9331A could not be predicted from the mutations known to be responsive because splice site mutations can lead to incorrect processing of mRNA precursors, including exon skipping or splicing at cryptic splice points, resulting in gross structural and functional alterations. While not wishing to be bound to any particular theory, it is thought that pharmacological chaperones are effective by enhancing the activity of the small amounts of wild-type enzyme produced. The synthesis, folding and trafficking of the wild-type enzyme may not be completely efficient. The pharmacological chaperone may stabilize the wild-type.

Treatment of a patient having the G9331 mutation or another splice site mutation in intron 4 is expected to result in amelioration of one or more of the symptoms described above. Treatment progress can be evaluated and monitored by tracking certain parameters. For example, as discussed above, one clinical marker that can be assessed for Fabry disease is the prevalence of deleterious cardiovascular manifestations. Cardiac complications are common in Fabry disease and are the main cause of death. The most frequent cardiac manifestation is LVH, which is an important risk factor for cardiac events. Reduction of LV-mass has been shown to improve outcomes in these patients. Migalastat treatment for up to 24-months significantly reduced LVMi, with larger decreases seen in patients with baseline LVH. The effect of ERT on LV-mass appears to be inconsistent. In a recent study, LVMi continued to increase in men >30 years of age treated with ERT. Another ERT study found that the initial improvement in LVMi diminished over time. As indicated by stable left ventricular posterior wall thickness and the decrease in intraventricular septal wall thickness, the reduction in LVMi in migalastat-treated patients in our study was not due to fibrosis. This reduction in LVMi is expected to contribute to a decrease in the cardiac complications that are common in Fabry disease.

Progressive decline in renal function is also a major complication of Fabry disease. For example, patients associated with a classic Fabry phenotype, which is associated with progressive renal impairment that can lead to dialysis or renal transplantation. The Chronic-Kidney-Disease-Prognosis-Consortium, eGFRCKD-EPI decline has been shown to be a reliable surrogate for subsequent risk of end-stage-renal disease and mortality.

Another method for monitoring treatment is to follow lyso-$GB_3$ (globotriaosylsphingosine) as a biomarker. Lyso-$GB_3$ is normally increased in patients with the disease, and can be detected in the urine. Thus, successful treatment of a patient will be marked by a decrease in the amount of lyso-$GB_3$.

Formulation and Administration

The dose and dosing regimen of pharmacological chaperone (e.g., DGJ) administration may vary depending on the patient since there is so much heterogeneity among mutations, and depending on the patient's residual α-GAL activity. As non-limiting examples, the following doses and regimens are expected to be sufficient to increase α-GAL in most "rescuable" individuals: 25 mg twice a day (b.i.d); 50 mg once a day; 50 mg b.i.d.; 50 mg once every other day, 75 mg once a day; 75 mg b.i.d.; 100 mg once a day; 100 mg b.i.d.; 150 mg once a day; 150 mg b.i.d., 150 mg once every other day; 250 mg once a day; 250 mg b.i.d. and 250 mg once every other day. In specific embodiments, the doses are 50 mg once a day; 50 mg once every other day; 150 mg once a day; 150 mg once every other day. In one or more embodiments, these doses pertain to 1-deoxygalactonojirimycin hydrochloride or an equivalent dose of 1-deoxygalactonojirimycin or a salt thereof other than the hydrochloride salt. In some embodiments, these doses pertain to the free base. In alternate embodiments, these doses pertain to a salt of 1-deoxygalactonojirimycin. In further embodiments, the salt of 1-deoxygalactonojirimycin is 1-deoxygalactonojirimycin hydrochloride. It is noted that 150 mg of 1-deoxygalactonojirimycin hydrochloride is equivalent to 123 mg of the free base form of 1-deoxygalactonojirimycin. Thus, in one or more embodiments the dose is 150 mg once every other day of 1-deoxygalactonojirimycin hydrochloride or an equivalent dose of 1-deoxygalactonojirimycin or a salt thereof other than the hydrochloride salt. In further embodiments, the dose is 150 mg once every other day of 1-deoxygalactonojirimycin hydrochloride. In other embodiments, the dose is 123 mg once every other day of the 1-deoxygalactonojirimycin free base.

Administration of DGJ according to the present invention may be in a formulation suitable for any route of administration, but is preferably administered in an oral dosage form such as a tablet, capsule or solution. As one example, the patient is orally administered capsules each containing 25 mg, 50 mg, 75 mg, 100 mg or 150 mg 1-deoxygalactonojirimycin hydrochloride or an equivalent dose of 1-deoxygalactonojirimycin or a salt thereof other than the hydrochloride salt.

In particular embodiments, the dose of SPC (e.g., 1-deoxygalactonojirimycin or salt thereof) is from about 25 mg to about 250 mg 1-deoxygalactonojirimycin hydrochloride or an equivalent dose of 1-deoxygalactonojirimycin or a salt thereof other than the hydrochloride salt. In further embodiments, the dose of SPC (e.g., 1-deoxygalactonojirimycin hydrochloride) is about 150 mg every other day. In some embodiments, the SPC (e.g., 1-deoxygalactonojirimycin or salt thereof) is administered orally. In one or more embodiments, the SPC (e.g., 1-deoxygalactonojirimycin or salt thereof) is administered by injection. The SPC may be accompanied by a pharmaceutically acceptable carrier, which may depend on the method of administration.

In one embodiment of the invention, the chaperone compound is administered as monotherapy, and can be in a form suitable for any route of administration, including e.g., orally in the form tablets or capsules or liquid, in sterile aqueous solution for injection, or in a dry lyophilized powder to be added to the formulation of the replacement enzyme during or immediately after reconstitution to prevent enzyme aggregation in vitro prior to administration.

When the chaperone compound is formulated for oral administration, the tablets or capsules can be prepared by conventional means with pharmaceutically acceptable excipients such as binding agents (e.g. jpregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

The pharmaceutical formulations of the chaperone compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified enzyme and the chaperone compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The route of administration of the chaperone compound may be oral (preferably) or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant).

Embodiments relating to pharmaceutical formulations and administration may be combined with any of the other embodiments of the invention, for example embodiments relating to a method of treating a patient with Fabry disease, a method of enhancing α-galactosidase A in a patient diagnosed with or suspected of having Fabry disease, use of a pharmacological chaperone for α-galactosidase A for the manufacture of a medicament for treating a patient diagnosed with Fabry disease or to a pharmacological chaperone for α-galactosidase A for use in treating a patient diagnosed with Fabry disease as well as embodiments relating to amenable mutations, the SPCs and suitable dosages thereof.

In one or more embodiments, chaperone is administered in combination with enzyme replacement therapy. Enzyme replacement therapy increases the amount of protein by exogenously introducing wild-type or biologically functional enzyme by way of infusion. This therapy has been developed for many genetic disorders including lysosomal storage disorders Fabry disease, as referenced above. After the infusion, the exogenous enzyme is expected to be taken up by tissues through non-specific or receptor-specific mechanism. In general, the uptake efficiency is not high, and the circulation time of the exogenous protein is short. In addition, the exogenous protein is unstable and subject to rapid intracellular degradation as well as having the potential for adverse immunological reactions with subsequent treatments. In one or more embodiments, the chaperone is administered at the same time as replacement enzyme. In some embodiments, the chaperone is co-formulated with the replacement enzyme.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in various embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

EXAMPLES

Example 1: Effect of DGJ on G9331A Mutation

The effect of DGJ in a male Fabry lymphoblast line with confirmed presence of the G9331A GLA mutation was studied to determine the magnitude and $EC_{50}$ values. G9331A or normal human (positive control) lymphoblasts were seeded at 25,000 cells per well (in 96-well plates). The lymphoblasts were then incubated±DGJ (10-point concentration-response curves) for 5 days. The concentration range for both cell lines was 5 nM to 100 μM. The α-Gal A activity in cell lysates was measured using the 4-MUG synthetic fluorogenic substrate. Maximum levels in the presence of DGJ are defined as the top of the sigmoidal concentration-response curve. It was then determined if α-Gal A levels were increased in response to DGJ. Enzyme assay results were confirmed by western blot.

Figure 5:
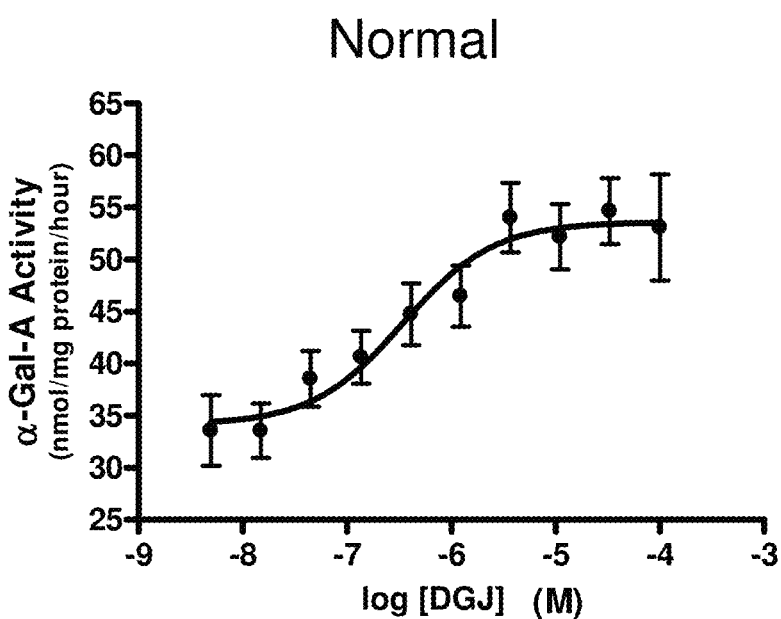
FIG. 5 shows the α-Gal A activity in control lymphoblasts exposed to DGJ.

FIGS. 4 and 5 show representative α-Gal A activity data in mutant and normal lymphoblasts, respectively. As seen in the figures, both the G9331A and normal positive control lymphoblasts show concentration-dependent increased levels in response to DGJ. Data points are the mean±SEM of quadruplicate determinations. The data represent the results of four independent experiments.

A summary of the α-Gal A activity is shown in Table 1 below.

TABLE 1

Lymphoblast α-Gal A activity data summary

| | | −DGJ | | +DGJ | | | | % of WT | Relative | |
| --- | --- | --- | --- | --- | --- | --- | --- | --- | --- | --- |
| Cell Line | N | α-Gal A activity | % of WT | α-Gal A activity | % of WT | Relative Increase | $EC_{50}$ (μM) | @ 10 μM DGJ[#] | Increase @ 10 μM DGJ[#] | T-test |
| Normal | 4 | 36 ± 6 | 100 ± 0 | 58 ± 7 | 167 ± 10 | 1.6 ± 0.1*** | 0.52 ± 0.2 | 164 | 1.6 | 0.0008 |
| G9331A | 4 | 6.2 ± 1 | 19 ± 5 | 9.8 ± 1.2 | 31 ± 6 | 1.6 ± 0.2* | 0.63 ± 0.3 | 30 | 1.6 | 0.0155 |

α-Gal A activity, nmol/mg protein/hr;
% of WT, percent of wild-type α-Gal A activity without AT1001;
Columns with the symbol "#" indicate that the values at 10 μM AT1001 are calculated based on the measured baseline, maximum and $EC_{50}$ values using a sigmoidal concentration-response equation that assumes a Hill slope of 1 (maximum levels in the presence of AT1001 are defined as the top of the sigmoidal concentration-response curve);
*p < 0.05,
**p < 0.01,
***p < 0.001 by two-tailed, paired t-test comparing baseline and maximum α-Gal A activity.

As shown in Table 1, for this 'leaky splice site' mutation, the G9331A lymphoblasts have lower than normal baseline α-Gal A activity. However the maximum relative increase and $EC_{50}$ value are virtually equivalent to those of normal lymphoblasts. In addition, significant increases in α-Gal A protein levels, similar to those of normal lymphoblasts, were seen in response to DGJ incubation of this Fabry cell line (G9331A, 2.1±0.5-fold, n=3; Wild Type, 1.8±0.1-fold, n=6). The results from the IVS4+919G→A lymphoblasts meet the HEK-293 cell criteria for an 'eligible mutation': α-Gal A mutant forms with a relative increase that is 1.2-fold above baseline and an absolute increase that is ≥3% of wild-type after incubation with 10 μM DGJ.

Figure 6:
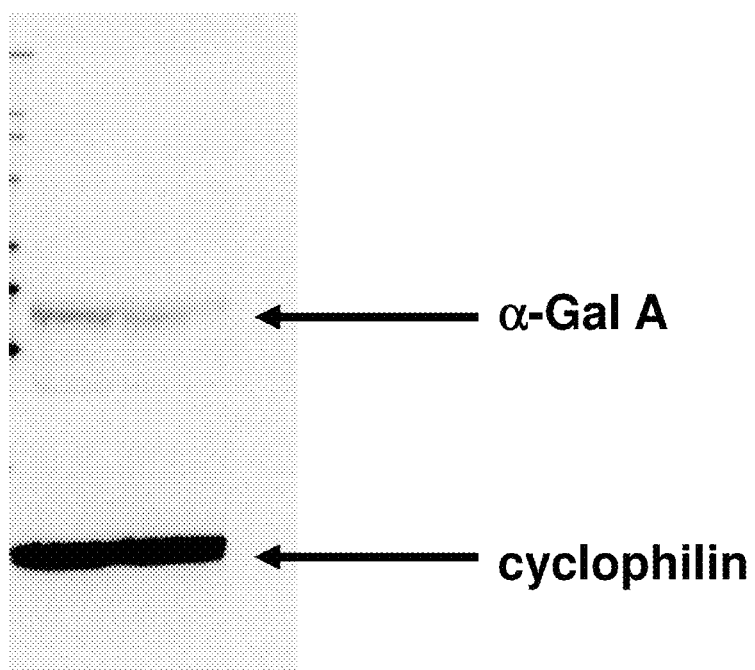
FIG. 6 is a Western blot showing α-Gal A activity in mutant lymphoblasts with and without incubation with DGJ.

Western blot data was used to confirm the previous results. 40 μg lysate was loaded per lane. Representative Western blot data of the G9331A lymphoblasts is shown in FIG. 6. As seen in the figure, the Western blot demonstrated an increase in α-Gal A protein of ~1.68-fold after incubation with 1 mM DGJ. This data represent the results of four independent experiments.

Example 2: Verification of G9331 Mutation

The presence of G9331A was confirmed in the cell line by sequencing. A 1000-bp fragment surrounding the site of the IVS4+919G→A mutation was PCR amplified from genomic DNA isolated from the mutant (tested two different cultures) or normal human lymphoblasts (wild-type). Each fragment was sequenced (Genewiz), and the presence of the IVS4+919G→A mutation was confirmed in both lots of G9331A cells whereas the wild-type sequence was confirmed in the normal cells.

Example 3: Verification of Absence of Wild-Type GLA in G9331 Lymphoblasts

Next, it was verified that the wild-type GLA gene is not present in the tested mutant lymphoblasts. Three separate strategies were used to demonstrate that the wild-type GLA gene is not present in the G9331A lymphoblasts. In all three strategies, G9331A lymphoblast samples were compared to those of wild-type lymphoblasts and a 1:1 G9331A:wild-type mixture. Samples from wild-type lymphoblasts were used as a control to show that the method is sensitive for detection of the pure wild-type gene. Samples from the mixture of mutant and wild-type lymphoblasts were used as a control to show that the method is sensitive for detection of the wild-type gene at a level expected from a heterozygous female (because no female G9331A lymphoblasts are available)

Strategy 1: PCR Amplification of a Y Chromosome-Specific Gene

Figure 7:
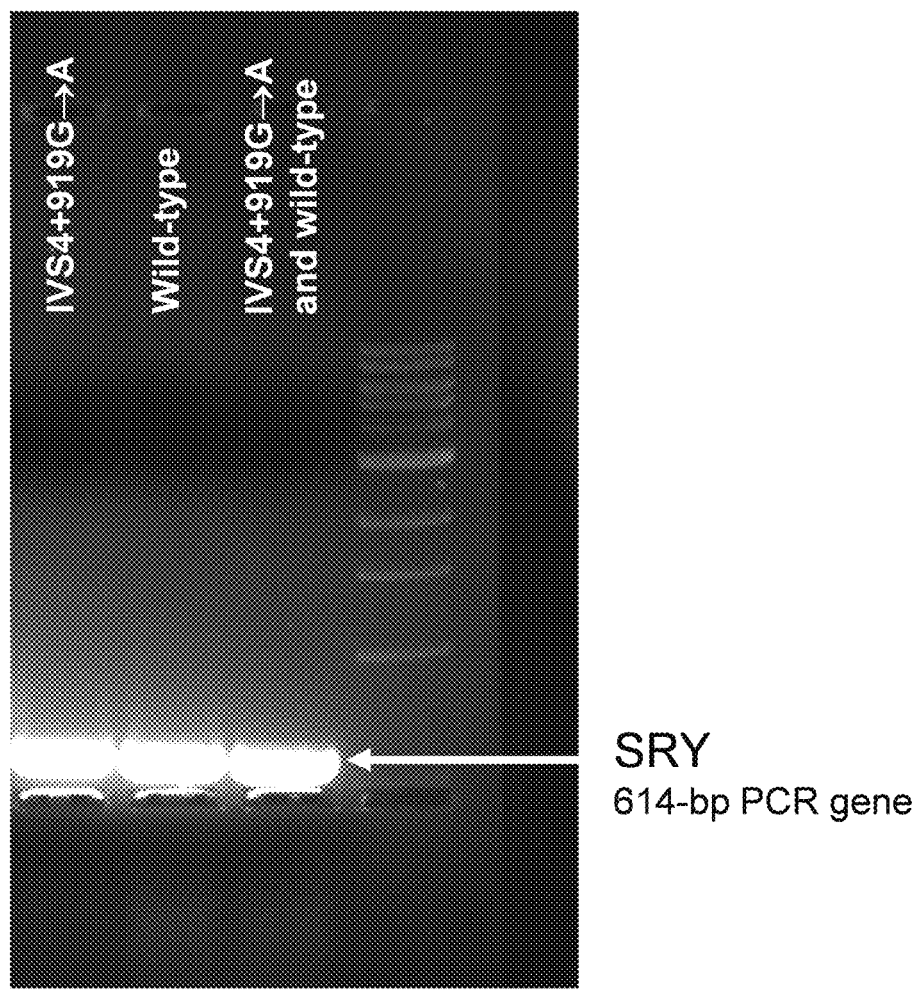
FIG. 7 is an electrophoresis gel showing the presence of an SRY gene.

Under this strategy, absence of wild-type GLA is confirmed if the cell line is from a male. If the cell line is from a male, then only the mutant allele can be present. SRY (sex-determining region Y, 614-bp; ACC #L08063) was chosen as the Y chromosome-specific gene to PCR amplify. SRY was readily amplified from the IVS4+919G→A lymphoblasts (FB-11 cell lines), indicating that the genomic DNA from these cells contains a Y chromosome. SRY was also readily amplified from wild-type lymphoblasts (wild-type cell line) and from a 1:1 mixture of genomic DNA from the two cell lines, indicating that the wild-type genomic DNA also contains a Y chromosome. The results of this experiment are shown in FIG. 7, where the presence of SRY in all three samples is clearly shown. In summary, these results indicate that the IVS4+919G→A lymphoblast cell line is male Strategy 2: Demonstrate the Absence of a Bfa I Restriction Site at G9331A In this strategy, the absence of a Bfa I restriction site at G9331A in a PCR-amplified fragment of genomic DNA indicates absence of wild-type GLA gene. The G9331A mutation disrupts a Bfa I cleavage site that is present in the wild-type GLA gene (see Ishii et al, Am J Hum Genet 70:994-1002, 2002).

A 334-bp PCR fragment surrounding IVS4+919 was amplified from lymphoblast genomic DNA, digested with Bfa I, and analyzed by agarose gel electrophoresis. A G→A transition mutation at IVS4+919 removes a Bfa I recognition site. If wild-type GLA is present, then three bands are expected (334, 122 and 212 bp). If IVS4+919G-→A is present, then only one band is expected (334 bp).

Figure 8:
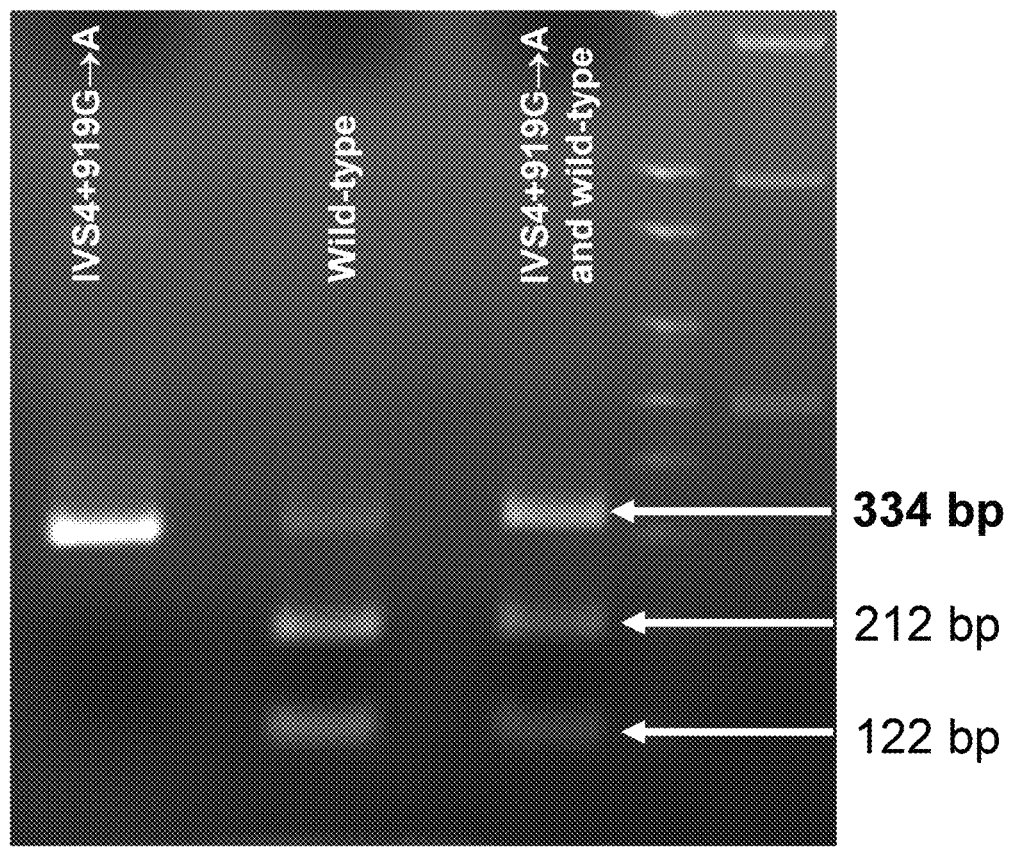
FIG. 8 is an electrophoresis gel showing the presence or absence of a Bfa I restriction site.

The results are shown in FIG. 8. As shown in the figure, Bfa I digestion was detected in samples from control wild-type lymphoblasts and from a 1:1 mixture of genomic DNA from the two cell lines. No Bfa I digestion was detected in IVS4+919G→A lymphoblasts, indicating that no wild-type GLA gene was present in the genomic DNA of these cells.

Figure 9:
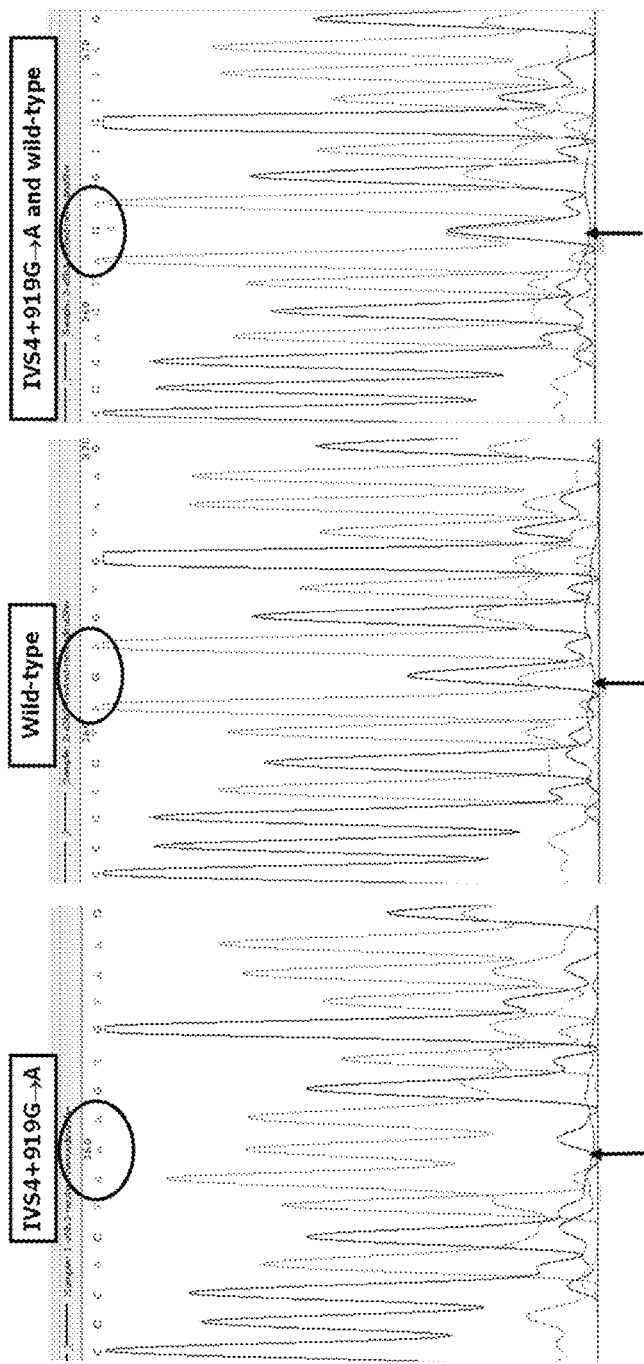
FIG. 9 shows the sequencing of three amplified PCR fragments from lymphoblast genomic DNA.

Strategy 3: Show Optimal Sequencing Results that Indicate the Pure Presence of G9331A Using this strategy, optimal sequencing results are generated that clearly show the pure presence of the mutant "A" nucleotide without any hint of the wild-type "G." First, a 1962 bp PCR-fragment was amplified from lymphoblast genomic DNA using gene-specific primers and high fidelity polymerase, Next, a 721 bp PCR-fragment was amplified using internal primers within the 1962 bp fragment. Three PCR samples were sent to GeneWiz for DNA sequencing. The results, shown in FIG. 9, suggest that only "A" is present in the sample, only "G" is present in the wild-type sample, and both "A" and "G" are present in the mixed sample This suggests that no wild-type GLA gene is present in the genomic DNA of IVS4+919G→A lymphoblasts

SUMMARY AND CONCLUSIONS

As shown in the above examples, the α-Gal A activity assessed in the assay and by western blots show that α-Gal A levels are increased in response to DGJ in G9331A lymphoblasts. Further, the magnitude of the response to DGJ meets the Fabry pharmacogenetic reference table criteria for an "eligible mutation." Further, the response was confirmed to be solely from α-Gal A produced from IVS4+919G→A GLA, as the cells were shown to be male and no evidence of a wild-type GLA allele was detected from the genomic DNA in these cells. This shows that cells with the G9331A splice site mutation will respond to treatment with chaperone, and therefore Fabry patients with this genotype may be selected for treatment with DGJ.

What is claimed is:

1. A method of treating a patient diagnosed with Fabry disease, the method comprising administering to the patient a therapeutically effective dose of 1-deoxygalactonojirimycin or salt thereof, wherein the patient has a splice site mutation in the nucleic acid sequence encoding α-galactosidase A and the patient expresses at least some wild-type α-galactosidase A.

2. The method of claim 1, wherein the mutation is relative to SEQ ID NO: 1.

3. The method of claim 1, wherein the mutation is a splice site mutation in intron 4 of the nucleic acid sequence encoding α-galactosidase A.

4. The method of claim 1, wherein the dose of 1-deoxygalactonojirimycin or salt thereof is from about 25 mg to about 250 mg.

5. The method of claim 1, wherein the salt of 1-deoxygalactonojirimycin is 1-deoxygalactonojirimycin hydrochloride.

6. The method of claim 1, wherein the dose is about 150 mg every other day of 1-deoxygalactonojirimycin hydrochloride or an equivalent dose of 1-deoxygalactonojirimycin or a salt thereof other than the hydrochloride salt.

7. The method of claim 1, wherein the 1-deoxygalactonojirimycin or salt thereof is administered orally.

8. The method of claim 1, wherein the 1-deoxygalactonojirimycin or salt thereof is administered by injection.

9. The method of claim 1, where in the patient is male.

10. The method of claim 1, where in the patient is female.

11. A method of treating a human patient diagnosed with Fabry disease, the method comprising administering to the patient a therapeutically effective dose of 1-deoxygalactonojirimycin or salt thereof, wherein the patient has a splice site mutation in the nucleic acid sequence encoding α-galactosidase A and the patient expresses at least some wild-type α-galactosidase A, and wherein the dose is about 25 to about 250 mg every other day of 1-deoxygalactonojirimycin hydrochloride, or an equivalent dose of 1-deoxygalactonojirimycin or a salt thereof other than the hydrochloride salt.

12. The method of claim 11, wherein the mutation is relative to SEQ ID NO: 1.

13. The method of claim 11, wherein the mutation is a splice site mutation in intron 4 of the nucleic acid sequence encoding α-galactosidase A.

14. The method of claim 11, wherein the dose is about 150 mg every other day of 1-deoxygalactonojirimycin hydrochloride or an equivalent dose of 1-deoxygalactonojirimycin or a salt thereof other than the hydrochloride salt.

15. The method of claim 11, wherein the salt of 1-deoxygalactonojirimycin is 1-deoxygalactonojirimycin hydrochloride.

16. The method of claim 11, wherein the 1-deoxygalactonojirimycin or salt thereof is administered orally.

17. The method of claim 11, wherein the 1-deoxygalactonojirimycin or salt thereof is administered by injection.

18. The method of claim 11, where in the patient is male.

19. The method of claim 11, where in the patient is female.

* * * * *

SEQUENCE LISTING

<160> NUMBER OF SEQ ID NOS: 3

<210> SEQ ID NO 1
<211> LENGTH: 12436
<212> TYPE: DNA
<213> ORGANISM: Homo sapiens

<400> SEQUENCE: 1
cccttctgta ggggcagaga ggttctactt cattactgcg tctcctggga aggccatcag    60
gactgctggc taaagtggga accaggactc tttgtgagtt aagaatttgt gtatttatat   120
gtgtgttata cacatttttt aaaaaactgt aacgacatca ggttgagcag tcgtctccgg   180

```
gtggtgaatt atgtgtattt ttaaatttta tactatattg ttattttttca aatgttcgaa      240
attgaatatg tagattgttg ttatcagcag aaaaataaac attattcaaa tactctattc      300
agtaaagtaa tttattgggc gcctttgtca agcacgcatt tgcctagatg tgactctaca      360
gataaaattc acttgggcc tccccttaca gacaatcagg cagtggagac tgagtgcctg       420
aatggataga ccagcactca gaccactatt ttcagtatct gttttctta actcagggcc       480
gtggttttca aacgttttc gccttacggt cacccttagg gtccccgag accgcccag         540
acagacagat atacaaaaac acatacacag tcatgagcgt ccaccatttc cccaccaggc      600
gcagcacagg cggcttcccg gcactgagat gggggggagg agggagagag cgcgaggggg      660
gaggggaaag cagagaacga agaggcgga ggcggcccc gaaccccgct ctggtcttca        720
tcatcaccac ccctgggtcc ccagttccca cccacacacc aacctctaac gatacccgggt    780
aattttcctc cttcttccct caaacggcta tagcgagacg tagacgacg accagaacta      840
cttctgctca cgtaagcgag taatcacgtg agcgcctacg tcatgtgaga tctcggtcac     900
gtgagcaact ctcggcttaa actcgggatc actaaggtgc cgcacttcct tctggtatgg    960
aaatagggcg ggtcaatatc aagaaggaa gagggtgatt ggttagcgga acgtcttacg    1020
tgactgatta ttggtctacc tctggggata accgtcccag ttgccagaga acaataacg    1080
tcattattta ataagtcatc ggtgattggt ccgcccctga ggttaatctt aaaagcccag    1140
gttacccgcg gaaattatg ctgtccggtc accgtgacaa tgcagctgag aacccagaa     1200
ctacatctgg gctgcgcgct tgcgcttcgc ttcctggccc tcgtttcctg ggacatccct    1260
gggctagag cactggacaa tggattggca aggacgccta ccatgggctg gctgcactgg    1320
gagcgcttca tgtgcaacct tgactgccag gaagagccag attcctgcat caggtatcag    1380
atattgggta ctccttccc tttgcttttc catgtgtttg ggtgtgtttg gggaactgga    1440
gagtctcaac gggaacagtt gagcccgagg gagagctccc ccacccgact ctgctgctgc    1500
ttttttatcc ccagcaaact gtcccgaatc aggactagcc ctaaactttc tctgtgtgac    1560
cttttcctggg atgggagtcc ggccagcggc ccctgtttct ttctctctct ctctctctct    1620
cgttctcctt ctctttctct ttctcttctt tcctctctct ttctctctct ccctgcccgg    1680
ttctcttttt tcactgctcc ttgcagagca gggccacccc ataggcagtg tgcccaaagt    1740
agccctgccc ggttctattc agaccctttct tgtgaacttc tgctcttcct ctgccgggtg    1800
ctaaccgtta gaacatctag ggtgggtagg aggaatgggg aactaagatt cgtgccattt    1860
tttctccttt tggggtcgtg gatttctcgg cagtatctcg agggagttag agagaccata    1920
aggtcgctga gatctctccc acctcgccca tgagcgtggc atcaggctgg aaggttgaca    1980
tggaggaact ttatacattt acacctttgc gtgagggttg aggctggatt agataggtat    2040
tgaacatatc tgaccctcac aatccttatc tgtaaattgg gattacaacc tttttaattc    2100
agggagctga caaaaaaaat ctgaaaaata gttcttatct cacacaggtg agttttcaag    2160
gagataacct atttaaagta catagcacag cgcttgacca ttcaactgcg cttacagagc    2220
aaatgttcaa tgggaaaatg aatgtaaatc tacaaatctg aatgaatatg tgtatttttc    2280
tggagagagt atatttacct ttcttcaaat tctcaaaggg ctctgtgatt taaaaaaggt    2340
taggaatcac tgatagatgt tggtaaaagg tggcagtcac agtacatttc tgtgtccata    2400
agttattcct atgaatatct ttatagataa agtcaggatg ttggtcagac atcacagaag    2460
aaattggcct tgtaagtttc atgtgaccct gtggtacagt atgtgtggca attttgccca    2520
tcacggattt tttttttattg gtatttgcat ctgattataa aactaatgca tgatcattgc    2580
```

```
aaaaaatgta gataaagaag agcaaaatga aaataaagat ttcccccac cgttccacca      2640 cccagaaata atcatggttt aaatgttaat atacaacctt acaattgttt tctatataaa      2700
tgaaaacata gatttcttta tttcattatt ttccataaaa aatggatcat gtttatgtca      2760
tgtttggcta atggcaagac cctggcaccc agtctgggct caaattctgc ctcattgtta      2820
cttagccctg tgacattggg taaattacac tttttttttt tttttttttt tgagacgggg      2880
tctcgctctg tcgcccaggc tggagtgcag tggcacgatc tcggctcact gcaagtccgc      2940
ctcctgggtt cacgccattc ttctgcctca gcctcccgag tagctgggac tacaggcgcc      3000
tgccaccacg cctggctctt tttttttttt tttttttttt tagtacagac ggggtttcac      3060
catgttagcc aggtggtct caatctcctg acctcgtgat tcgcccgcct cagcctccca      3120
aagtgctggt gtgagccacc gtgcccagcc ttactttttt ttttgagagg gggtctcact      3180
ctgtcaccca ggttggagtg cagtggcgcg atctctgctc agtgcaaact ccacctcccg      3240
ggtttaagca gttctcctgt cgtagtctcc tgagtagctg ggattacagg cacaccacca      3300
cggccagcta atttttgtat tttcagtaga gacgggtttc accatgttgc ccaagctggt      3360
ctcgaactcc tggcctcaag tgatctgccc gccttggcct cccagagtgc tgggattaca      3420
ggtgtgagcc accgcacccg gcctcttttt tcttttttag tctatcatac cttgcaaata      3480
cagtggttct tcctatgtgt tggttttgat atttatgtaa tcaaacacat cagttttcc      3540 tttctgattt ctgactttgg ggtcatgctg agaaagtcct ttcctacctg aagataatac      3600
agtatatacg tttcttacta gtattttgt ggattttaa aatatttaaa tctttagtcc      3660
atctgaactt gttcttctat cagaaatgcc acatttaata aataataagt cccatggtat      3720
cagatggctg gaaggacctc tttcgaaact ttgtttaatt ccattaatct gtgtattctt      3780
attctaatgc taatagttcc acactagctt cctttatctt ttttttcttt tttttttttt      3840
ttttgagctg gagtttcgct cttgttgccc aggctggagt acaatgtcac gatctcggtt      3900
caccgcaacc tccgcctccc aggttcaagc aattctcctg cctcatcctc gcgagtagct      3960
ggaattacag gcatgcgcca ccacgcctag ctattttgta ttttagtag agatggggtt      4020 tctccatgtt ggtcaggctg gtctcaaact cccagcctca ggtgatctgc ctgcctcggc      4080
ctcccaaaat gctgttatta caggcgtgag ccaccacgcc cagccttcat ctttttaatga      4140 atgtacatgt atgtaatctt ttaggtgaac ttttttgtaat gttgtgccaa gttccttaaa      4200
aagccctttt ggaagctggg caggtggcca cgcctgtaat cccagcattt gggagtctg      4260 aggcaggtgg atcacttgag gccaggagtt caagactagc ctagccaaaa tgcaaaaccc      4320
tgtctctact aaagatacaa aaattagccg gatgcgatgg cacatgcctg taatctcagc      4380
tactcgggag gctgaggtag aagaatcgct tgaaccgggg aggcagaggt tgcagtgagc      4440
aagatggcgc cactgcactc cagcctgggt gacagaggga gactccatct caaaaaaaaa      4500
aaaaaaaaaa aagataaaaa ggaaacctaa gtactcttgg gctttgttaa ggattttgtt      4560
aaatatacaa aggattgcag ggaaaattaa cttatttta atattgagta tgcttatcca      4620
agagcaaaat aatatttctc catttattca aatcatttag gagcatcata gttttaacat      4680
atgggccttg cacgtatctt aaatttatct ctaggcattt taggttgttc agttgttctt      4740
gtgaatggga tcttttttctc caaataggat tattgttgat atctgttgat tatgttaact      4800
ttgtagtttc tgactttact gaactgtctt cttagatcta atactctttt caatttcatc      4860
atatatttct cattcctatt ttgtttgggg tttttagggc gggaatatta acgggataag      4920
```

```
agagacaaaa gaaaatctgg aaaaacaatt cattttacct tacattgctt gtgattacta    4980
ccacactatt actgggttgg aaaaaattgt gaaatcccaa ggtgcctaat aaatgggagg    5040
tacctaagtg ttcatttaat gaattgtaat gattattgga atttctcttt cagtgagaag    5100
ctcttcatgg agatggcaga gctcatggtc tcagaaggct ggaaggatgc aggttatgag    5160
tacctctgca ttgatgactg ttggatggct ccccaaagag attcagaagg cagacttcag    5220
gcagaccctc agcgctttcc tcatgggatt cgccagctag ctaattatgt gagtttatag    5280
ataatgttct tgttcattca gaggactgta agcacttctg tacagaagct tgtttagaaa    5340
cagccctcat ggccgggcgt ggtggctcac gctgtaatcc caacactttg ggaggccgag    5400
gcgggtggat cacctgaggt caagagttca agaccagcct ggccaacatg gtgaaacccc    5460
aactctatta aaagtacaaa aaattagctg gcatggtgg tgaacgcctg taaccccagc     5520
tacttgggag gctgaggcag gagaatcgct tgaacccagg aggtggaagt tcagtgagc     5580
tgagatcacg ccattgcact ctagcctggg caacaaaaga gaaactccat ctcaaaaaaa    5640
aaaacaagga aaaaagaaa cagccctcat gacacttaga aagtagaata gctggctgtt     5700
atctgaacat tgaattgtaa ggcttatcag gtggactttg cattccatca gcagacaatt    5760
tttttttttt tttttttttg agatggagtc tcattctgtc tcccaggctg gagggcagtg    5820
gtgcgatctc ggctcactgc aagctccacc tcctgggttc atgccattct cctgcctcag    5880
cctcccaagt agctgggacc acaggcaccc gccaccatgc ccagtaatt tttgtattt      5940
ttagtagaga cggggtttca ccatgttagc caagatggtc tcgatctcct gacctcgtga    6000
tccgcccacc tcggcctccc aaagtgctgg gattacaggc atgagccacc gcgcctagcc    6060
tacaaatgtt ttgtaatagc tcttgaggcc catcttggag ttctcctttt gctaaaacca    6120
ctgaactctc taggaggaaa aaggaacttg gttcttgaca tatgtgtgca tgtatttcca    6180
tataaccttt aggaagctat tgcaatggta ctataaacta gaattttaga agatagaagg    6240
aaaatattct ggagatcatt gaagagaaat ggagtccaac actagttaaa gatgatgaag    6300
acagattttt ttttttgacg gagtctcgct ctgtcgccca ggctggagtg cagtggcaca    6360
atctcagctc actgcaaccc tccacctctt gggttcaagt gattctcctg cctcagcctc    6420
ccaagtagct gggactacag gcgcacacca ccacgcccgg ctaattttg tatttttagt     6480
agagacaagg tttcaccata ttcgccaggc tggtctcgaa ctcctgacct tgtaatccgc    6540
ccaccttggc ctcccaaagt gctgggatta caggcatgag ccaccacgcc cggccgatga    6600
agacagattt tattcagtac taccacagta gaggaaagag ccaagttcaa ttccaaatac    6660
aacaaagaca ggtggagatt tatagccaat gagcagattg agggggtcag tggatggaat    6720
atttaagaag acatcaaggg tagggagctt cttgctaaag cttcatgtac ttaaacaaga    6780
agggtggggg atgagggaaa ttgatcagat atcaatggtg gcagtattga cttagcagga    6840
ttcttgctaa gaggtcttgc taggacagac ataggaagcc aaggtggagg tctagtcgaa    6900
aagaaggctc atcagagaag tctaactaaa gtttggtcaa gaagagtctt tgtcaaggta    6960
aatctatcat ttccctcaaa aggtaatttt caggatccca tcaggaagat tagcatggct    7020
gctagctttc tcctcagttc tgggctatag ctcacatgcc tagtttgaac tagctcagca    7080
gaactggggg atttattctt tgtcttccaa caaactcatc tggatgattt tggggggtttg    7140
tggggaaaag cccccaatac ctggtgaagt aaccttgtct cttcccccag cctggaatgg    7200
ttctctcttt ctgctacctc acgattgtgc ttctacaatg gtgactcttt tcctccctct    7260
catttcaggt tcacagcaaa ggactgaagc tagggattta tgcagatgtt ggaaataaaa    7320
```

```
cctgcgcagg cttccctggg agttttggat actacgacat tgatgcccag acctttgctg   7380
actggggagt agatctgcta aaatttgatg gttgttactg tgacagtttg gaaaatttgg   7440
cagatggtaa tgtttcattc cagagattta gccacaaagg aaagaacttt gaggccatgg   7500
tagctgagcc aaagaaccaa tcttcagaat tttaaatacc ctgtcacaat actggaaata   7560
attattctcc atgtgccaga gctcccatct cttctctttc agttcattaa ttaattaatt   7620
aattcatgta aaatccatgc ataccctaacc atagctaata ttgtgcactt ataattcaag   7680
agggctctaa gagttaatta gtaattgtaa ctctctataa catcatttag gggagtccag   7740
gttgtcaatc ggtcacagag aaagaagcat cttcattcct gcctttcctc aatatacaca   7800
ccatctctgc actacttcct cagaacaatc ccagcagtct gggaggtact ttacacaatt   7860
taagcacaga gcaactgcct gtccctgctg ctagtttaaa catgaacctt ccaggtagcc   7920
tcttcttaaa atatacagcc ccagctgggc atgatggctc atgcctgtaa tcctagcact   7980
ttgggaggct gaggcgggtg gattacttga ggtcaggagt tcgagaccac cctggccaac   8040
atggtgaaac cccatctcta gtaaaaatac aaaaattagc tgactttggt ggcacatgcc   8100
tgtaatccca gctacttggg aagctgagac agaagagtca cttgaacctg ggaaacagag   8160
gttgcagtga gccaagatcg caccactgca ctccaccctg gatgacagac tgaaccccat   8220
ctcaaaaaat taaaataaaa taaaataaaa taactatata tatagcccca gctgaaaatt   8280
catttctttc ccttatttta cccattgttt tctcatacag gttataagca catgtccttg   8340
gccctgaata ggactggcag aagcattgtg tactcctgtg agtggcctct ttatatgtgg   8400 cccttttcaaa aggtgagata gtgagcccag aatccaatag aactgtactg atagatagaa   8460
cttgacaaca aaggaaacca aggtctcctt caaagtccaa cgttacttac tatcatccta   8520
ccatctctcc caggttccaa ccacttctca ccatccccac tgctgtaatt atagcctaag   8580
ctaccatcac ctggaaagtc atccttgtgt cttcccctt atttcaccat tcatgtcctg   8640
tctatcaaca gtccttccac cagtatctct aaaatatctc ctgaatcagc ccacttcctt   8700
ccatcttcac tacatgcacc ctggccttcc aagctactat cggctctcaa ccagactgct   8760
gggaccacct gatctctctg cttccactct gtctcaaccc ccatctattt tccaagcagc   8820
actagagtta tcatattaaa atgtaaatat cagtttttt tttaaagaaa aaaccctga   8880 gacttaacag agtaaaaaa aatataaatg tcatcatcag ttccctgctt aaaacccta   8940 actcgcttcc aattgcactt ggaatgaaac caaactgcac tgatccagcc cttgcctgcc   9000
tccccaaagt ccaaggggtc atggctcttt ccctggctac actggttttc tttctgtccc   9060
tcaacactgc aagcctattg ctgccccagg gcctttacac ttgcttttt tctgcctaga   9120 acagttcttc cccaaagatt tttaaagggc cgggctcctt aacattgaag tcgcagacca   9180
aacgccacat atgcagacag ttcttctcta actactttaa aatagccctc tgtccattca   9240
ttcttcatca cattaacctg tttaattttc ttctcagagc tccacactat ttggaagtat   9300
ttgttgactt gttaccatgt ctccccacta gagtgtaagt ttcatgaggg cagggacctt   9360
gtctgacttt gactgtatct ctcgcatatg gttaagtgtt aaatagttat ttatggaatg   9420
aatccctatt attccctcat tatctctgca aaatagtctt ttttctcaac atcttaaacc   9480
tgatatccca cctgcctatc tacaaacttt ttttttgcga cagagtctca ctgtcaccca   9540
ggctagagtg cagtggcgcc atctcggctc actgcaacct ccgcctcccg ggtttaagcg   9600
attctcttgc ctcagcctcc cagtagctgg gattataggc gtgcgctacc acatctggct   9660
```

```
aatttttgta ttttttagtag agatggtttc accatgttgg ccaggcttgt ctcgaactcc   9720
tgacctcaga tgatccacct gcctcggcct cccaaagtgc tgggattaca ggcatgagcc   9780
accgtgccca gcctctacaa acttttttatt ccattaacaa actatatgct gggatttaag   9840
ttttcttaat acttgatgga gtcctatgta attttcgagc ttttaatttt actaagacca   9900
ttttagttct gattatagaa gtaaattaac tttaagggat ttcaagttat atggcctact   9960
tctgaagcaa acttcttaca gtgaaaattc attataaggg tttagacctc cttatggaga  10020
cgttcaatct gtaaactcaa gagaaggcta caagtgcctc ctttaaactg ttttcatctc  10080
acaaggatgt tagtagaaag taaacagaag agtcatatct gttttcacag cccaattata  10140
cagaaatccg acagtactgc aatcactggc gaaattttgc tgacattgat gattcctgga  10200
aaagtataaa gagtatcttg gactggacat cttttaacca ggagagaatt gttgatgttg  10260
ctggaccagg gggttggaat gacccagata tggtaaaaac ttgagccctc cttgttcaag  10320
accctgcggt aggcttgttt cctatttttga cattcaaggt aaatacaggt aaagttcctg  10380
ggaggaggct ttatgtgaga gtacttagag caggatgctg tggaaagtgg tttctccata  10440
tgggtcatct aggtaacttt aagaatgttt cctcctctct tgtttgaatt atttcattct  10500
ttttctcagt tagtgattgg caactttggc ctcagctgga atcagcaagt aactcagatg  10560
gccctctggg ctatcatggc tgctcccttta ttcatgtcta atgacctccg acacatcagc  10620
cctcaagcca aagctctcct tcaggataag gacgtaattg ccatcaatca ggacccttg   10680
ggcaagcaag ggtaccagct tagacaggta aataagagta tatattttaa gatggcttta  10740
tatacccaat accaactttg tcttgggcct aaatctattt ttttcccttg ctcttgatgt  10800
tactatcagt aataaagctt cttgctagaa acattacttt atttccaaaa taatgctaca  10860
ggatcatttt aattttttcct acaagtgctt gatagttctg acattaagaa tgaatgccaa  10920
actaacaggg ccacttatca ctagttgcta agcaaccaca cttttcttggt ttttcaggga  10980
gacaactttg aagtgtggga acgacctctc tcaggcttag cctgggctgt agctatgata  11040
aaccggcagg agattggtgg acctcgctct tataccatcg cagttgcttc cctgggtaaa  11100
ggagtggcct gtaatcctgc ctgcttcatc acacagctcc tccctgtgaa aaggaagcta  11160
gggttctatg aatggacttc aaggttaaga agtcacataa atcccacagg cactgttttg  11220
cttcagctag aaaatacaat gcagatgtca ttaaaagact tactttaaaa tgtttatttt  11280
attgccaact actacttcct gtccaccttt ttctccattc actttaaaag ctcaaggcta  11340
ggtggctcat gcctgtaatc ccagcacttt gggaggctga ggcgggcaga tcacctgagg  11400
tcgggacttt gagacccgcc tggacaacat ggtgaaaccc catttctaat aaaaatataa  11460
aaattagcca ggtgtggtgg cgcacctgtg gtcccagcta ctctggggc tgaggcatga  11520
gaatcgcttg aacccgggag tggaggttgc attgagctga gatcatgcca cctcactcca  11580
gcctgggcaa caaagattcc atctcaaaaa aaaaaaaaaa gccaggcaca gtggctcatg  11640
cctggaatcc cagcactttt ggaagctgag gcaggcagat cacttgaggt taggatttca  11700
agaccagcct ggctaacata gtaaagccct gtctctacta aaaatacaaa aattagccag  11760
gtatggtggc gagcttctgt agccccagct actcaggaga ctgaggcagg agaatcactt  11820
gaacccggga agtgggggg tgcagtgacc caagatcacg ccactgcatt ccagcctggg  11880
caacagagca agactccatc tcaaaaaaaa aagttctatt tccttgaata aaattttccg  11940
aagtttaaac tttaggaata aaactattaa acccgtattt actcatccag atacccaccc  12000
cccttgttga gattctctcc caattatcaa aatgtgtagc atatttaact accaagagct  12060
```

```
aaacatcatt aagactgaaa tgtattaaga aggatgtata ggccaggcac ggtgtctcac   12120
gcctgtaatc ccaacacttt gggaggccaa gtcgggcgga tcacgaggtc aggagatgga   12180
gaccatcctg gccaacatgg tgaaaccccc tctctactaa aaatacaaaa attagccagg   12240
caggtggcag gcacctgtaa tcccagctac tccagaggct gaggcaggac aatcacttga   12300
acctgggagg cagaggctgc agtgagctga ggttgtacca attgcactcc agcctaggta   12360
acgagcaaca ctccatctca aaaaagaaa aaaaaaaga tgtataattt ggaactgtta   12420
agaggcattt taaaga                                                   12436
```

<210> SEQ ID NO 2
<211> LENGTH: 429
<212> TYPE: PRT
<213> ORGANISM: Homo sapiens

<400> SEQUENCE: 2

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300
```

```
Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
            325                 330                 335

Phe Glu Val Trp Glu Arg Pro Leu Ser Gly Leu Ala Trp Ala Val Ala
                340                 345                 350

Met Ile Asn Arg Gln Glu Ile Gly Gly Pro Arg Ser Tyr Thr Ile Ala
            355                 360                 365

Val Ala Ser Leu Gly Lys Gly Val Ala Cys Asn Pro Ala Cys Phe Ile
        370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
                420                 425

<210> SEQ ID NO 3
<211> LENGTH: 60
<212> TYPE: DNA
<213> ORGANISM: Homo sapiens

<400> SEQUENCE: 3
agagacaaaa aaaaatctgg aaaaacaatt cattttacct tacattgctt gtgattacta    60
```